US012710365B2

(12) United States Patent
Wang et al.

(10) Patent No.: US 12,710,365 B2
(45) Date of Patent: Aug. 18, 2026

(54) NUCLEIC ACID EXTRACTION AND FLUORESCENT PCR DETECTION SYSTEM

(71) Applicant: AUTOBIO LABTEC INSTRUMENTS CO., LTD., Zhengzhou (CN)

(72) Inventors: Chao Wang, Zhengzhou (CN); Peng Zhao, Zhengzhou (CN); Yaoji Liu, Zhengzhou (CN); Zhenkun Li, Zhengzhou (CN); Yang Pan, Zhengzhou (CN); Long Sun, Zhengzhou (CN); Cong Liu, Zhengzhou (CN)

(73) Assignee: AUTOBIO LABTEC INSTRUMENTS CO., LTD., Zhengzhou (CN)

( * ) Notice: Subject to any disclaimer, the term of this patent is extended or adjusted under 35 U.S.C. 154(b) by 601 days.

(21) Appl. No.: 18/265,418

(22) PCT Filed: Dec. 24, 2021

(86) PCT No.: PCT/CN2021/141193

§ 371 (c)(1),
(2) Date: Jun. 5, 2023

(87) PCT Pub. No.: WO2022/143456

PCT Pub. Date: Jul. 7, 2022

(65) Prior Publication Data

US 2024/0027347 A1 Jan. 25, 2024

(30) Foreign Application Priority Data

Dec. 29, 2020 (CN) ........................ 202011601009.X

(51) Int. Cl.
*G01N 21/64* (2006.01)
*B01L 7/00* (2006.01)
(Continued)

(52) U.S. Cl.
CPC ............ *G01N 21/6428* (2013.01); *B01L 7/52* (2013.01); *C12N 15/1006* (2013.01);
(Continued)

(58) Field of Classification Search
CPC ............... B01L 7/52; B01L 2200/0647; B01L 2200/16; B01L 2300/0672;
(Continued)

(56) References Cited

U.S. PATENT DOCUMENTS

2014/0193826 A1* 7/2014 Gajewski ............... C12Q 1/686 435/6.12
2019/0226010 A1 7/2019 Gajewski et al.

FOREIGN PATENT DOCUMENTS

CN 108865659 * 11/2018 ............ C12Q 1/686
CN 108865659 A 11/2018
(Continued)

OTHER PUBLICATIONS

Machine Translation of WO 2017/204274 A1 (Year: 2026).*
(Continued)

*Primary Examiner* — Michael L Hobbs
(74) *Attorney, Agent, or Firm* — Yue (Robert) Xu; Apex Attorneys at Law, LLP

(57) ABSTRACT

A nucleic acid extraction and fluorescent PCR detection system, comprising: an extraction strip, an extraction strip loading device for loading the extraction strip, a sample holder loading device for loading and unloading samples, an extraction strip transfer gripper for driving the extraction strip to move to a preset position, a nucleic acid extraction device for purifying the samples to obtain nucleic acids, a PCR detection device for performing fluorescent PCR detection on the nucleic acids, and a control device, wherein the extraction strip loading device, the sample holder loading device, the extraction strip transfer gripper, the nucleic acid
(Continued)

extraction device and the PCR detection device are all connected to the control device. The problems of relatively poor flexibility and relatively low detection efficiency of a nucleic acid extraction and detection system can be ameliorated, so that a sample detection process is more flexible and convenient.

12 Claims, 21 Drawing Sheets

(51) Int. Cl.
*C12N 15/10* (2006.01)
*G01N 35/00* (2006.01)
*G01N 35/10* (2006.01)

(52) U.S. Cl.
CPC ..... *G01N 35/0099* (2013.01); *G01N 35/1002* (2013.01); *B01L 2200/0647* (2013.01); *B01L 2200/16* (2013.01); *B01L 2300/0672* (2013.01); *B01L 2300/1805* (2013.01); *G01N 2035/00356* (2013.01)

(58) Field of Classification Search
CPC ........ B01L 2300/1805; C12N 15/1006; C12Q 1/6806; C12Q 1/686; G01N 21/6428; G01N 35/0098; G01N 35/0099; G01N 35/04; G01N 35/1002; G01N 35/1079; G01N 2035/00108; G01N 2035/00356; G01N 2035/041; G01N 2035/0436; G01N 2035/0465; Y02A 50/30
See application file for complete search history.

(56) References Cited

FOREIGN PATENT DOCUMENTS

| | | | | | |
|---|---|---|---|---|---|
| CN | 108998444 | A | | 12/2018 | |
| CN | 109337793 | A | | 2/2019 | |
| CN | 112694970 | A | | 4/2021 | |
| CN | 215924933 | U | | 3/2022 | |
| WO | 2012/012779 | A2 | | 1/2012 | |
| WO | WO-2017204274 | A1 | * | 11/2017 | ......... G01N 35/1011 |

OTHER PUBLICATIONS

Search Report dated Jun. 3, 2024 for European patent application No. 21914193.4.
International Search Report for PCT/CN2021/141193 mailed Mar. 28, 2022, ISA/CN.

* cited by examiner

NUCLEIC ACID EXTRACTION AND FLUORESCENT PCR DETECTION SYSTEM

This application is the national stage of international patent application No. PCT/CN2021/141193, titled "NUCLEIC ACID EXTRACTION AND FLUORESCENT PCR DETECTION SYSTEM", filed on Dec. 24, 2021, which claims the benefit of the priority to Chinese Patent Application No. 202011601009.X, titled "NUCLEIC ACID EXTRACTION AND FLUORESCENT PCR DETECTION SYSTEM", filed with the China National Intellectual Property Administration on Dec. 29, 2020, both of which are incorporated herein by reference thereto in their entireties.

FIELD

The present application relates to the technical field of molecular diagnosis, and in particular, to a nucleic acid extraction and fluorescent PCR test system.

BACKGROUND

Molecular diagnosis has the advantages of high sensitivity, good specificity, being instant and convenient, and has been widely used in clinical practice. The diagnosis of some items puts forward higher requirements for the automation, flexibility and throughput of an extraction system.

At present, for most of the nucleic acid extraction systems on the market, samples are fed in batches, but only a small number of test items are available at one time, and most of the processes such as supply of samples, supply of extraction reagent strips and discard of consumables are carried out manually, which can no longer meet the market demand of projects with a large number of diagnosis samples. The existing nucleic acid extraction system requires that the sample to be tested be coded in advance or scanned manually, and placed manually in a test position. The test process is complex, resulting in high manual labor intensity. In addition, the batch sampling method may result in the failure of timely test for newly added samples when it is required to test the newly added samples. The newly added samples can be tested only after the previous batch of samples have been tested, which results in poor flexibility and low test efficiency of the system.

Therefore, how to improve the flexibility and test efficiency of the nucleic acid extraction and test system is a technical problem to be solved urgently by those skilled in the art.

SUMMARY

In view of the above, an object of the present application is to provide a nucleic acid extraction and fluorescent PCR test system, which can effectively improve the flexibility and test efficiency of the nucleic acid extraction and test system, and make the sample test process more flexible and convenient.

In order to achieve the above objects, the following technical solutions are provided according to the present application.

A nucleic acid extraction and fluorescent PCR test system includes an extraction strip, an extraction-strip loading device which has a function of on-line adding the extraction strip and is configured to load the extraction strip, a sample-holder loading device which is configured to load and unload a sample, an extraction-strip transfer gripper which is configured to drive the extraction strip to move to a preset position, a nucleic-acid extraction device which is configured to refine the sample to obtain nucleic acid, a PCR test device which is configured to perform a fluorescent PCR test on the nucleic acid, and a control device.

The extraction-strip loading device, the sample-holder loading device, the extraction-strip transfer gripper, the nucleic-acid extraction device and the PCR test device are all connected to the control device.

Preferably, the extraction-strip loading device includes a passage and a pushing device configured to push the extraction strip to move in the passage.

One end of the passage is a gripping position for the extraction strip. The pushing device is movable transversely, and the pushing device is connected to the control device.

Preferably, the gripping position is provided with a jacking device configured to move up and down to separate the extraction strip, and the jacking device is connected to the control device.

Preferably, the sample-holder loading device includes a sample holder which is configured to load the sample, a loading pusher, an emergency pusher, a scanner, a transfer pusher and an unloading pusher, wherein the transfer pusher is configured to transfer the sample to a scanning position of the scanner and to move the sample after scanning to a sampling position, and the unloading pusher is configured to convey the sample after sampling to a sample recovery area.

The loading pusher, the emergency pusher, the scanner, the transfer pusher, and the unloading pusher are all connected to the control device.

Preferably, the extraction-strip transfer gripper includes an openable gripper device which is configured to grip the extraction strip, a gripper lifting device which is configured to drive the gripper device to move up and down, and a gripper transverse-movement device which is configured to drive the gripper lifting device to move transversely, wherein the gripper device is arranged on the gripper lifting device, and the gripper lifting device is slidably connected with the gripper transverse-movement device.

The gripper device, the gripper lifting device and the gripper transverse-movement device are all connected to the control device.

Preferably, the nucleic-acid extraction device includes a sealing-film piercing device which is configured to pierce through a sealing film of the extraction strip, a filling device which is configured to add the sample to be tested to the extraction strip, a reagent needle, a magnetic-bead washing device, a high-temperature dissociation device which is configured to perform high-temperature incubation on the sample, and a refined-solution magnetic-absorption device which is configured to perform magnetic absorption refinement on the sample to obtain a nucleic acid refined solution.

The reagent needle is configured to add a corresponding reagent into the extraction strip or a PCR tube and to add the nucleic acid refined solution of the extraction strip into the PCR tube.

Preferably, the sealing-film piercing device includes a piercer and a driving assembly, wherein the driving assembly is connected with the piercer; when the piercer moves to a piercing position, the piercer pierces through the sealing film of the extraction strip; and the driving assembly is connected to the control device.

Preferably, the filling device includes a sample needle configured to draw the sample and a sample moving device configured to drive the sample needle to move in space, wherein the sample needle is connected to the sample moving device, and the sample moving device is connected to the control device.

Preferably, the high-temperature dissociation device includes an incubation heating block which is configured to heat a reaction chamber of the extraction strip and a heating block driving device, wherein the incubation heating block is connected to the control device.

Preferably, the magnetic-bead washing device includes a detergent needle, a detergent driving device configured to drive the detergent needle to move in space, a magnet device configured to selectively apply a magnetic field to the reaction chamber of the extraction strip, and a magnet driving device configured to drive the magnet device to rotate.

The magnet driving device is connected to the magnet device, and the detergent needle is connected to the detergent driving device.

The magnet driving device and the detergent driving device are both connected to the control device.

Preferably, the nucleic acid extraction and fluorescent PCR test system further includes a refrigeration-reagent supply device which has a refrigeration function and is configured to provide different reagents.

Preferably, the nucleic acid extraction and fluorescent PCR test system further includes a discard device which is configured to recycle the discarded extraction strip, and the discard device is connected to the control device.

Preferably, the PCR test device includes a fluorescent PCR test device configured to perform various fluorescent PCR tests on the sealed PCR tube.

The fluorescent PCR test device is connected to the control device.

Preferably, the fluorescent PCR test device includes a housing, a photometry assembly and temperature control components, wherein the housing is provided with multiple test positions for placing the PCR tube, and each of the multiple test positions is provided with the corresponding temperature control component, so that the temperatures in the multiple test positions are independently controlled to rise or fall; wherein the photometry assembly and the temperature control components are both connected to the control device.

The photometry assembly includes a light source assembly which is configured to provide a test light source and a driving component which is configured to drive the light source assembly to move. The number of the light source assembly is plural, the multiple light source assemblies provide different types of light sources, and each light source assembly illuminates, driven by the driving component, the corresponding test position.

During using the nucleic acid extraction and fluorescent PCR test system according to the present application, first, the control device can control the extraction-strip loading device to automatically load the extraction strip and control the sample-holder loading device to load the sample to be tested, and then, the control device can control the nucleic-acid extraction device to operate to add the sample and the reagent required for the reaction into the extraction strip. The extraction strip is moved, and the refining operations such as incubation and washing are performed on the sample and the reagent in the extraction strip, so as to obtain the nucleic acid refined solution. Finally, the PCR test device is used to perform fluorescent PCR tests on the nucleic acid, and the test results can be fed back to the control device in real time. The position shift of the extraction strip among the devices can be achieved by the extraction-strip transfer gripper, and the spatial movement of the extraction strip can be achieved by controlling the extraction-strip transfer gripper, so that the extraction strip can reach the required position for corresponding operation and reaction. In this way, the automatic operation of the nucleic acid extraction and test can be achieved, which is beneficial to lowering the intensity of manual operation and improving the test efficiency of the system.

The extraction-strip loading device of the system has the function of on-line adding extraction strip, such that there is no need to immediately interrupt the on-going pushing and conveying of the previous extraction strip every time a new extraction strip is added, which is beneficial to improving the automation degree and the continuous conveying effect of the extraction-strip loading device, and is beneficial to improving the sample testing efficiency.

In summary, the nucleic acid extraction and fluorescent PCR test system according to the present application can effectively improve the flexibility and test efficiency of the nucleic acid extraction and test system, and make the sample test process more flexible and convenient.

BRIEF DESCRIPTION OF THE EMBODIMENTS

For illustrating the technical solutions in the embodiments of the present application or in the conventional technology more clearly, drawings referred to for describing the embodiments or the conventional technology will be briefly described hereinafter. It is apparent to those skilled in the art that the drawings in the following description are only some embodiments of the present application, and other drawings may be obtained on the basis of the provided drawings without any creative efforts.

Figure 1:
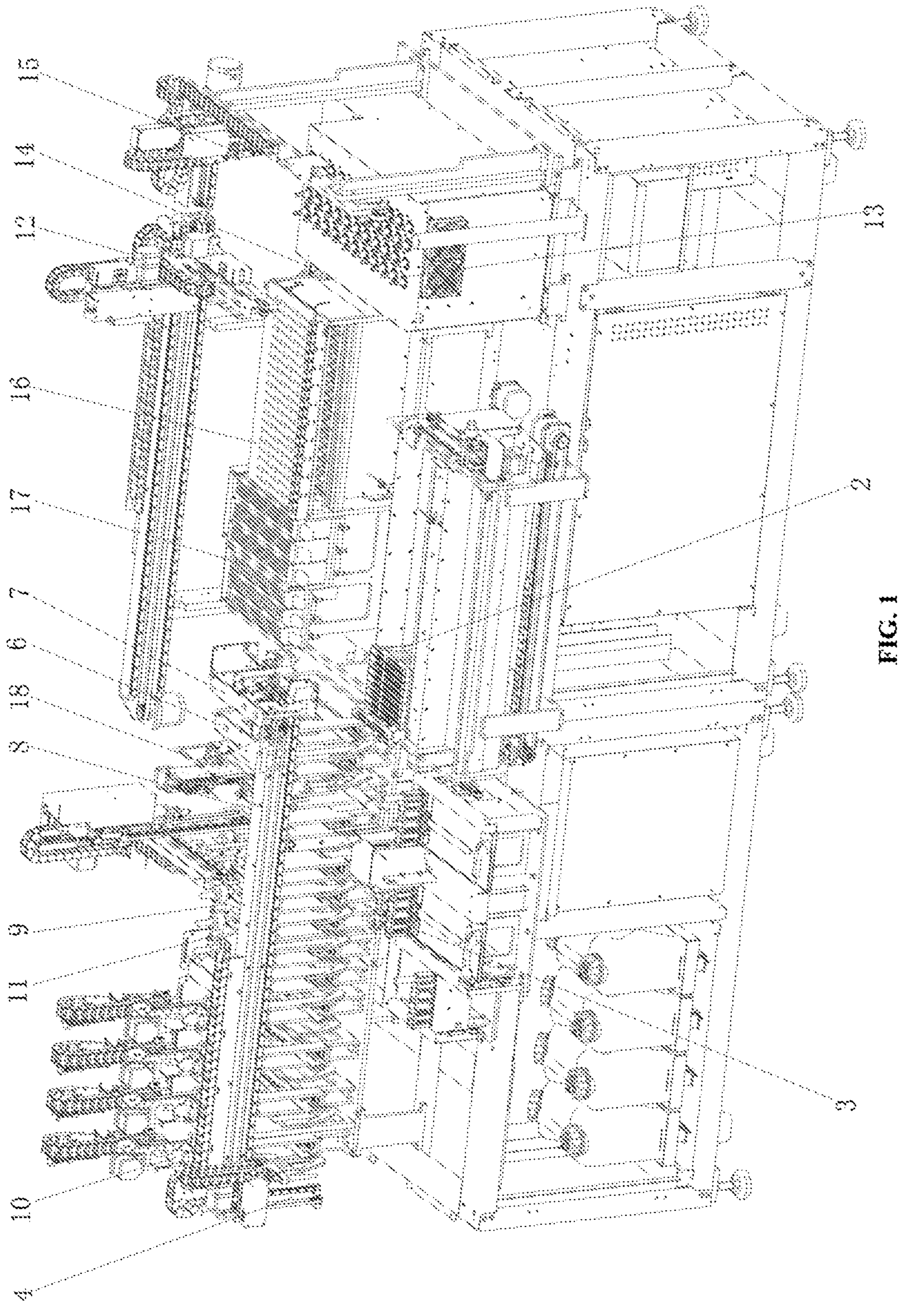
FIG. 1 is a schematic structural view of a nucleic acid extraction and fluorescent PCR test system according to the present application.

Reference numerals in FIGS. 1 to 21 are listed as follows:

1 extraction strip; 101 hanger; 102 TIP of 300 ul; 103 dissociation reagent; 104 identification; 105 detergent; 106 nucleic acid release liquid; 107 magnetic bead; 108 TIP of 2 ml; 109 reaction chamber;

2 extraction-strip loading device; 201 first passage; 202 second passage; 203 first pushing device; 204 second pushing device; 205 transfer device; 206 loading inlet; 207 gripping position; 208 jacking device; 209 avoidance hole;

3 sample-holder loading device; 301 sample holder; 302 loading pusher; 303 emergency pusher; 304 scanner; 305 transfer pusher; 306 unloading pusher; 307 sampling position;

4 extraction-strip transfer gripper; 401 gripper device; 402 gripper lifting device; 403 gripper transverse-movement device;

5 sample tube;

6 refined-solution magnetic-absorption device; 601 refinement forward-backward pusher; 602 magnet;

7 sealing-film piercing device; 701 piercer; 702 washing device; 703 piercing forward-backward pusher; 704 scanner;

8 filling device; 801 sample needle; 802 sample moving device; 8021 sample vertical movement manipulator; 8022 sample forward-backward movement manipulator; 803 first forward-backward pusher;

9 low-temperature lysis device; 901 second forward-backward pusher; 902 incubation heating block;

10 magnetic-bead washing device; 1001 detergent needle; 1002 detergent driving device; 1003 magnet device; 1004 fourth forward-backward pusher;

11 high-temperature dissociation device; 1101 third forward-backward pusher;

12 reagent needle; 1201 needle device; 1202 needle driving device; 12021 needle horizontal movement manipulator; 12022 needle forward-backward movement manipulator; 12023 needle vertical movement manipulator;

13 fluorescent PCR test device; 1301 photometry assembly; 1302 pressing cylinder; 1303 test position; 1304 pressing-cylinder placement position; 1305 PCR-tube discard port;

14 PCR-tube transfer device; 1401 PCR-tube placement hole; 1402 transfer block;

15 PCR-tube transfer gripper; 1501 PCR gripper; 1502 PCR horizontal movement manipulator; 1503 PCR forward-backward movement manipulator; 1504 PCR vertical movement manipulator;

16 refrigeration-reagent supply device; 1601 liquid draw hole;

17 consumable supply device; 1701 TIP consumable holder; 1702 PCR consumable holder; 1703 TIP; 1704 PCR tube; 1705 PCR cover;

18 discard device; 1801 waste liquid needle; 1802 openable gripper; 1803 fifth forward-backward pusher.

DETAILED DESCRIPTION OF THE EMBODIMENTS

Technical solutions in the embodiments of the present application are clearly and completely described hereinafter in conjunction with the drawings in the embodiments of the present application. Apparently, the embodiments described in the following are only some embodiments of the present application, rather than all embodiments. Any other embodiments obtained by those skilled in the art on the basis of the embodiments of the present application without any creative work fall within the scope of protection of the present application.

A core of the present application is to provide a nucleic acid extraction and fluorescent PCR test system, which can effectively improve the flexibility and test efficiency of the nucleic acid extraction and test system, and make the sample test process more flexible and convenient.

Reference is made to FIGS. 1 to 21.

A nucleic acid extraction and fluorescent PCR test system is provided according to a specific embodiment, which includes an extraction strip 1, an extraction-strip loading device 2 which has a function of on-line adding the extraction strip 1 and is configured to load the extraction strip 1, a sample-holder loading device 3 which is configured to load and unload one or more samples, an extraction-strip transfer gripper 4 which is configured to drive the extraction strip 1 to move to a preset position, a nucleic-acid extraction device which is configured to refine the sample to obtain nucleic acid, a PCR test device which is configured to perform a fluorescent PCR test on the nucleic acid, and a control device. The extraction-strip loading device 2, the sample-holder loading device 3, the extraction-strip transfer gripper 4, the nucleic-acid extraction device and the PCR test device are all connected to the control device.

Figure 2:
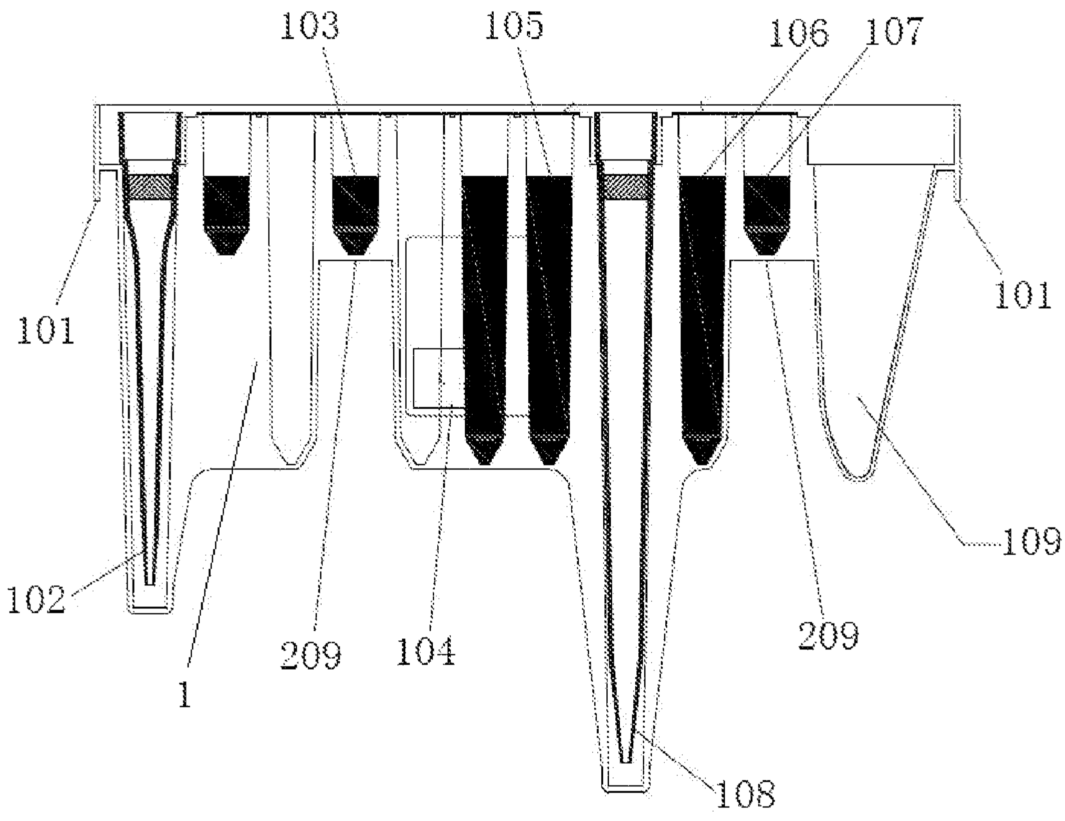
FIG. 2 is a schematic structural view of an extraction strip.
Figure 3:
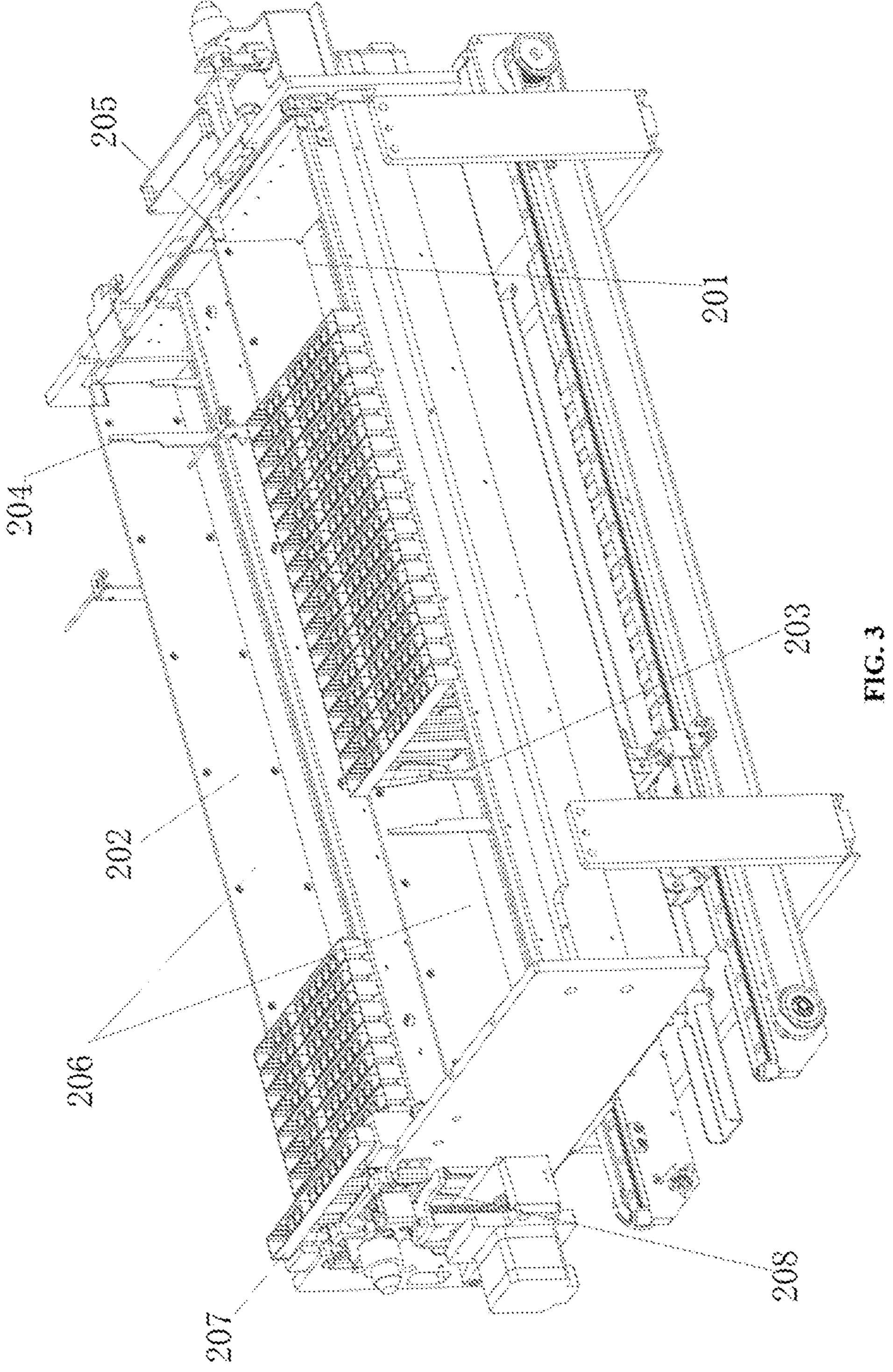
FIG. 3 is a schematic structural view of an extraction-strip loading device.
Figure 4:
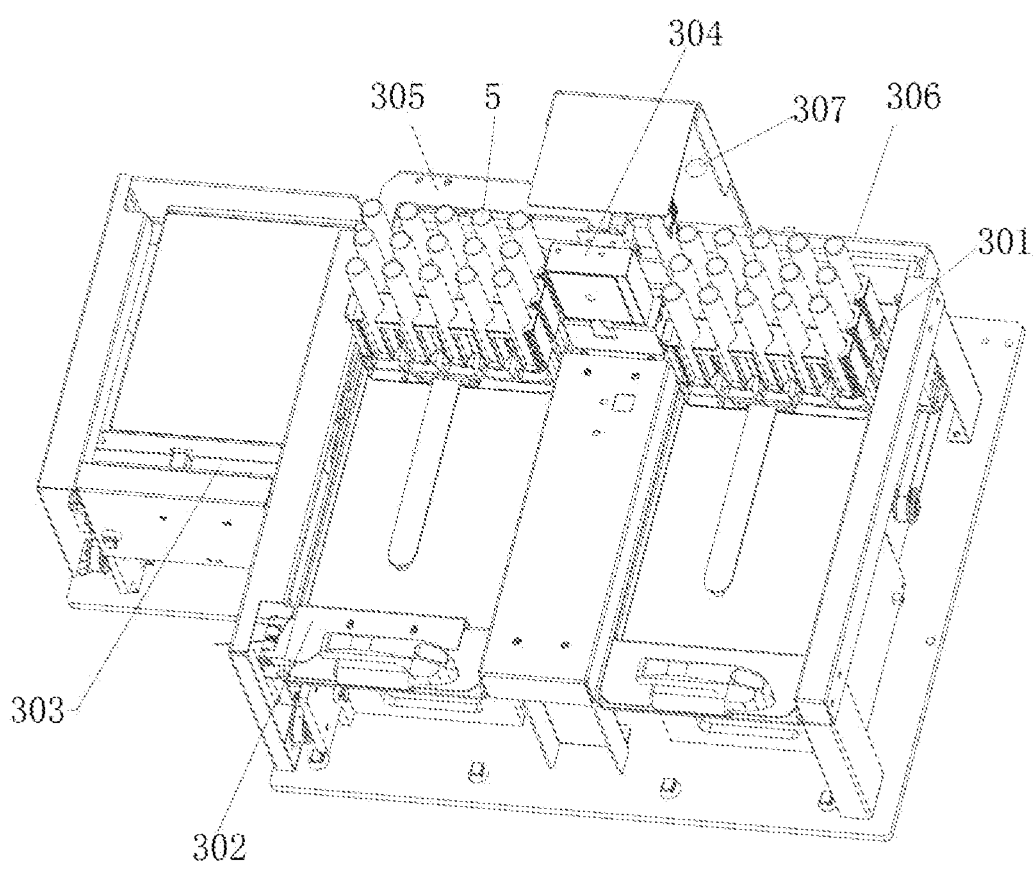
FIG. 4 is a schematic structural view of a sample-holder loading device.
Figure 5:
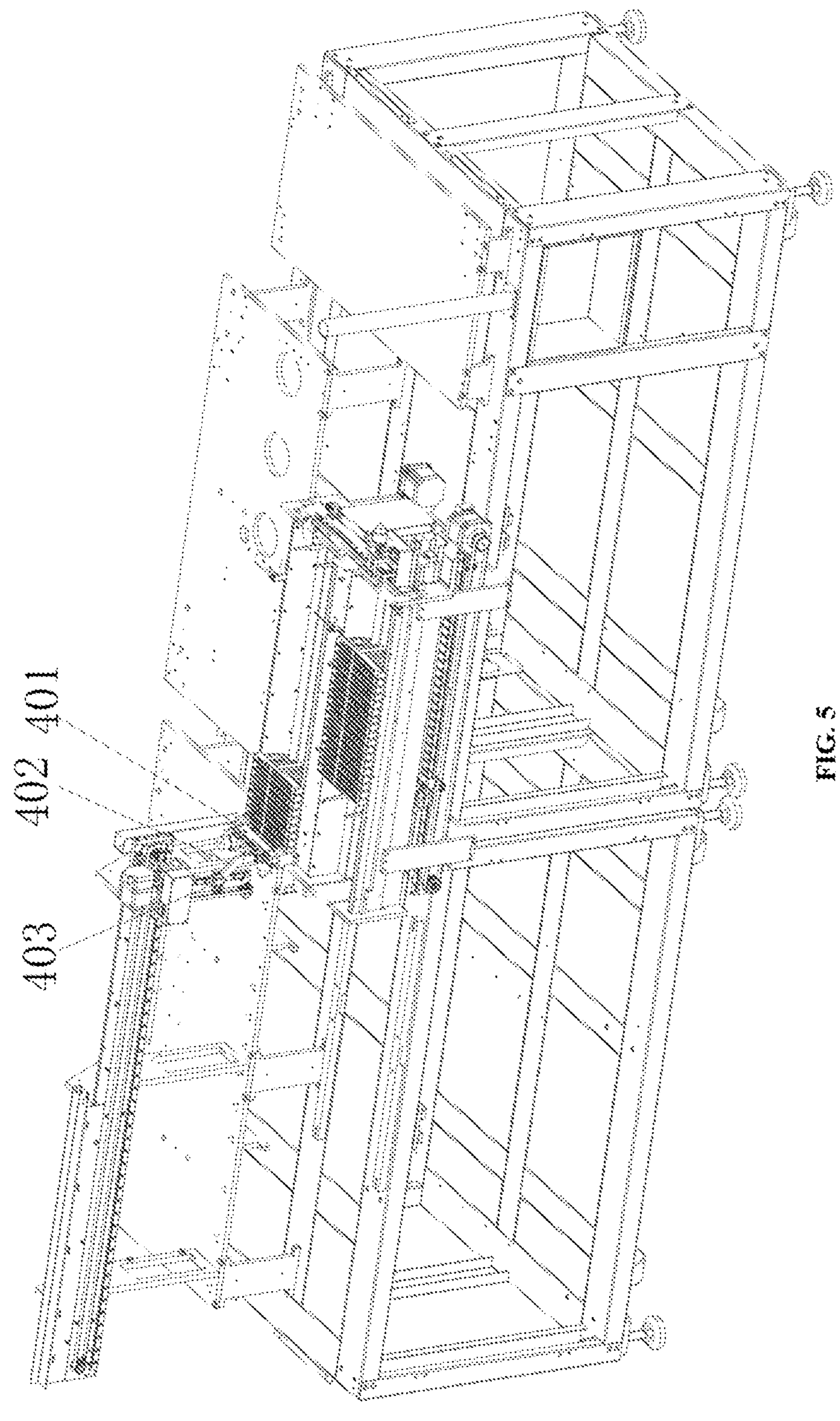
FIG. 5 is a schematic structural view of an extraction-strip transfer gripper.
Figure 6:
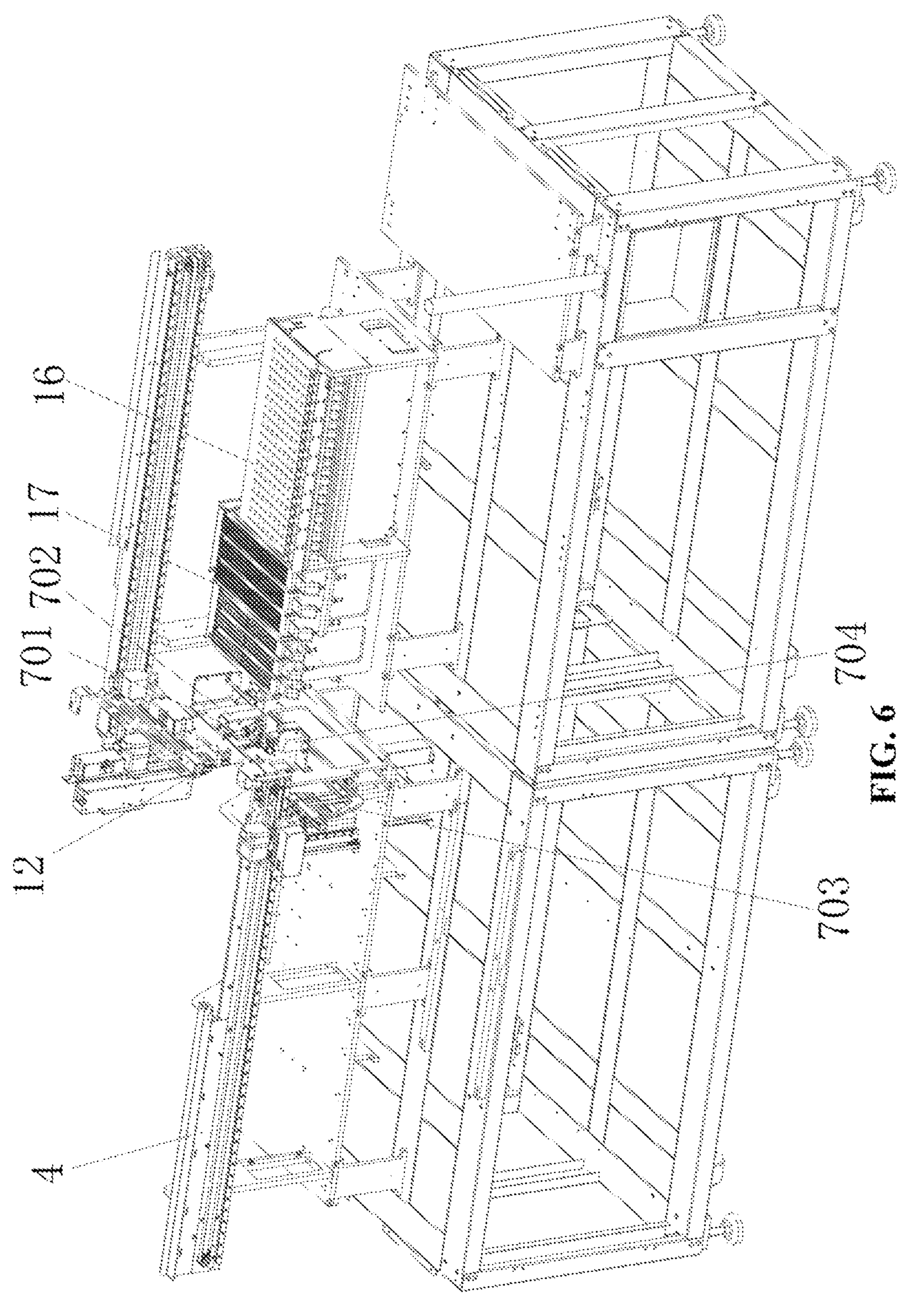
FIG. 6 is a schematic structural view of a sealing-film piercing device.
Figure 7:
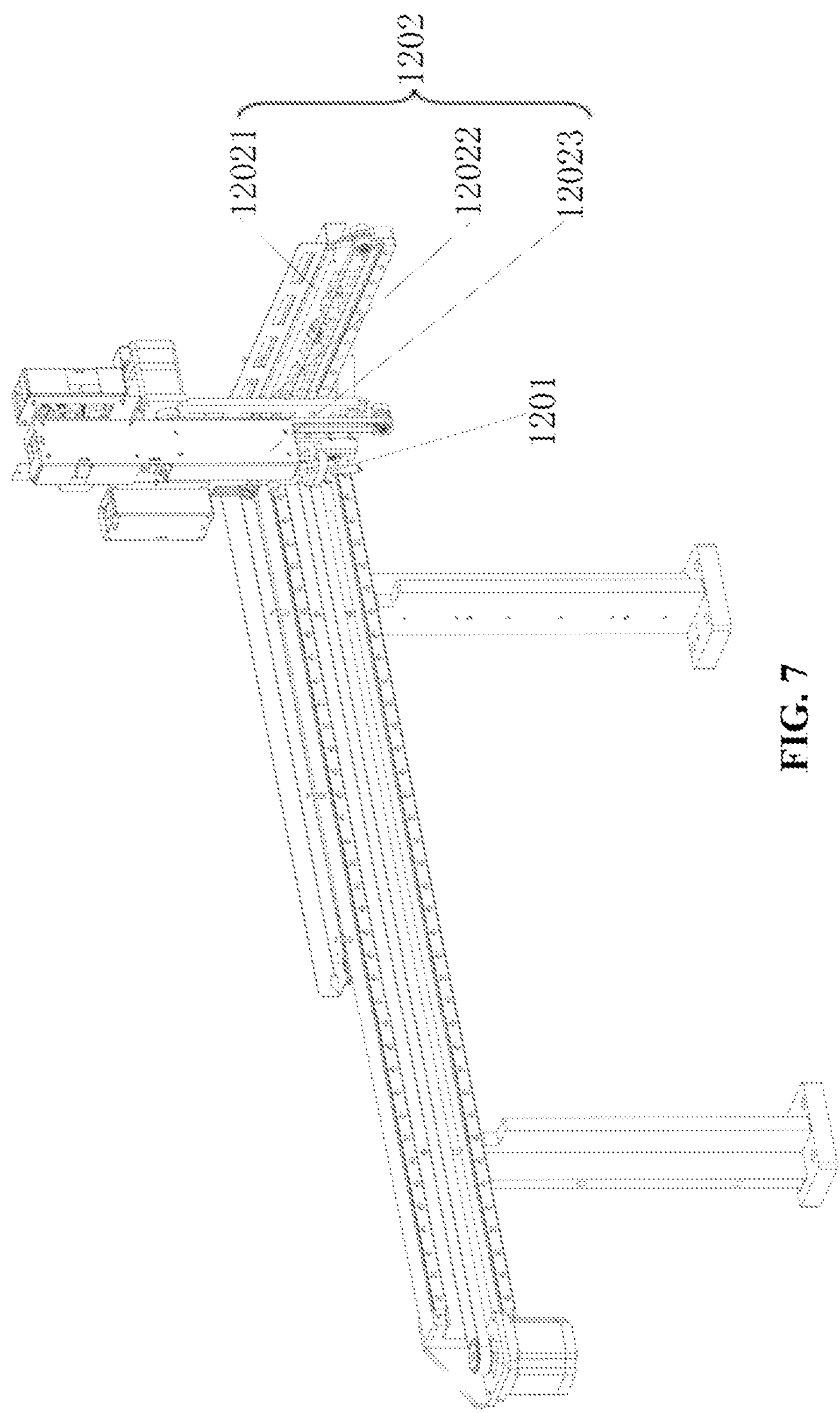
FIG. 7 is a schematic structural view of a reagent needle.
Figure 8:
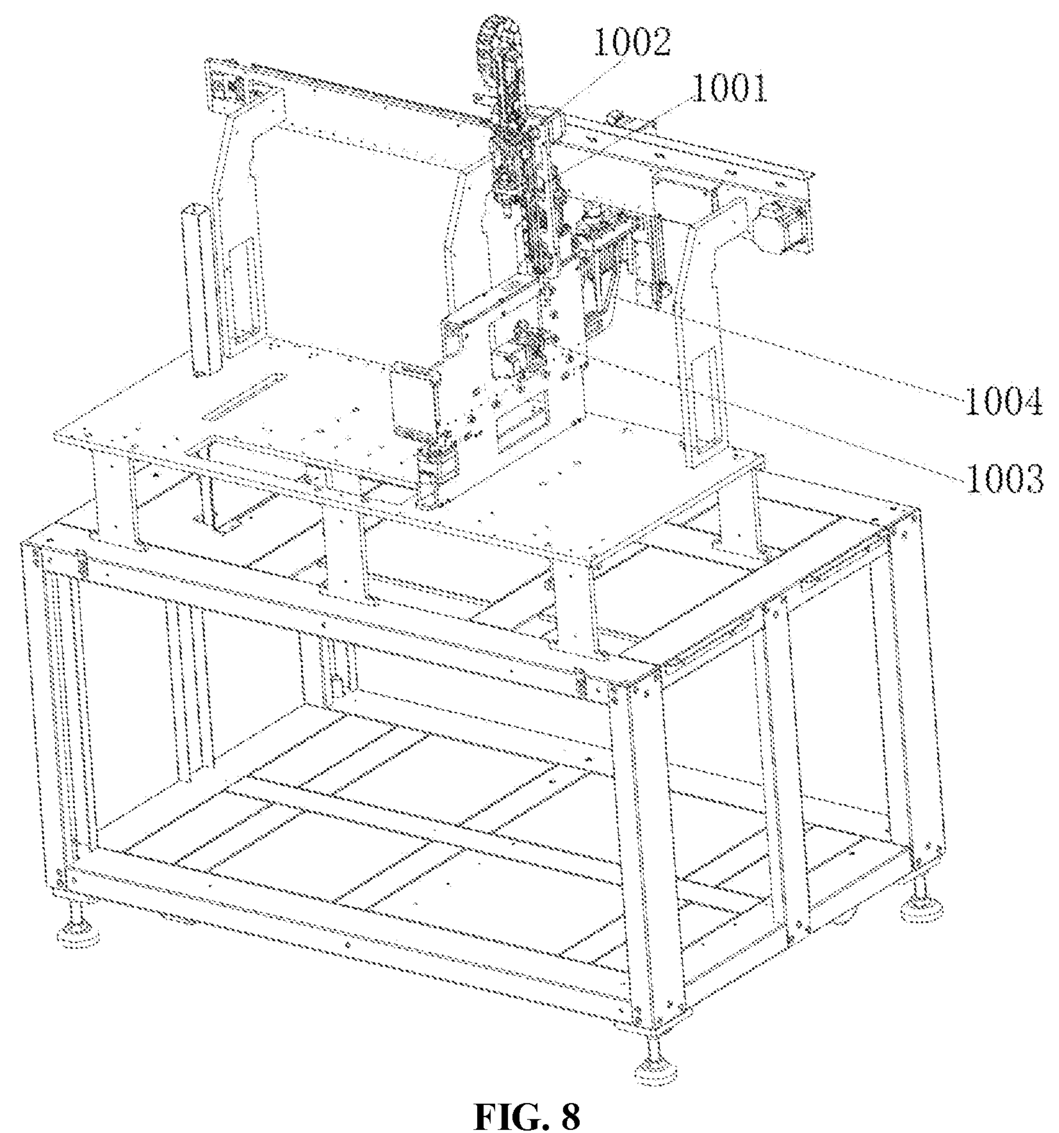
FIG. 8 is a schematic structural view of a magnetic-bead washing device.
Figure 9:
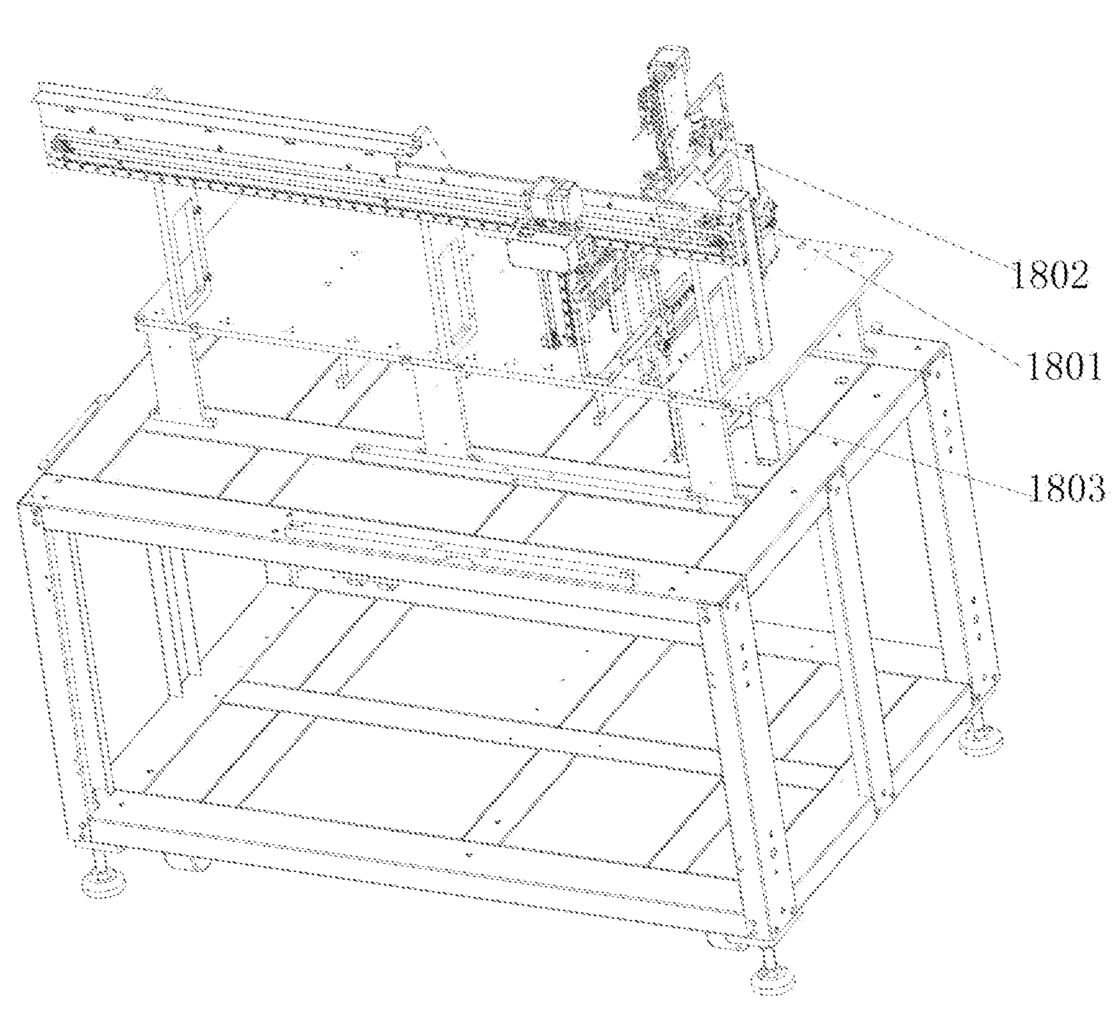
FIG. 9 is a schematic structural view of a discard device.
Figure 10:
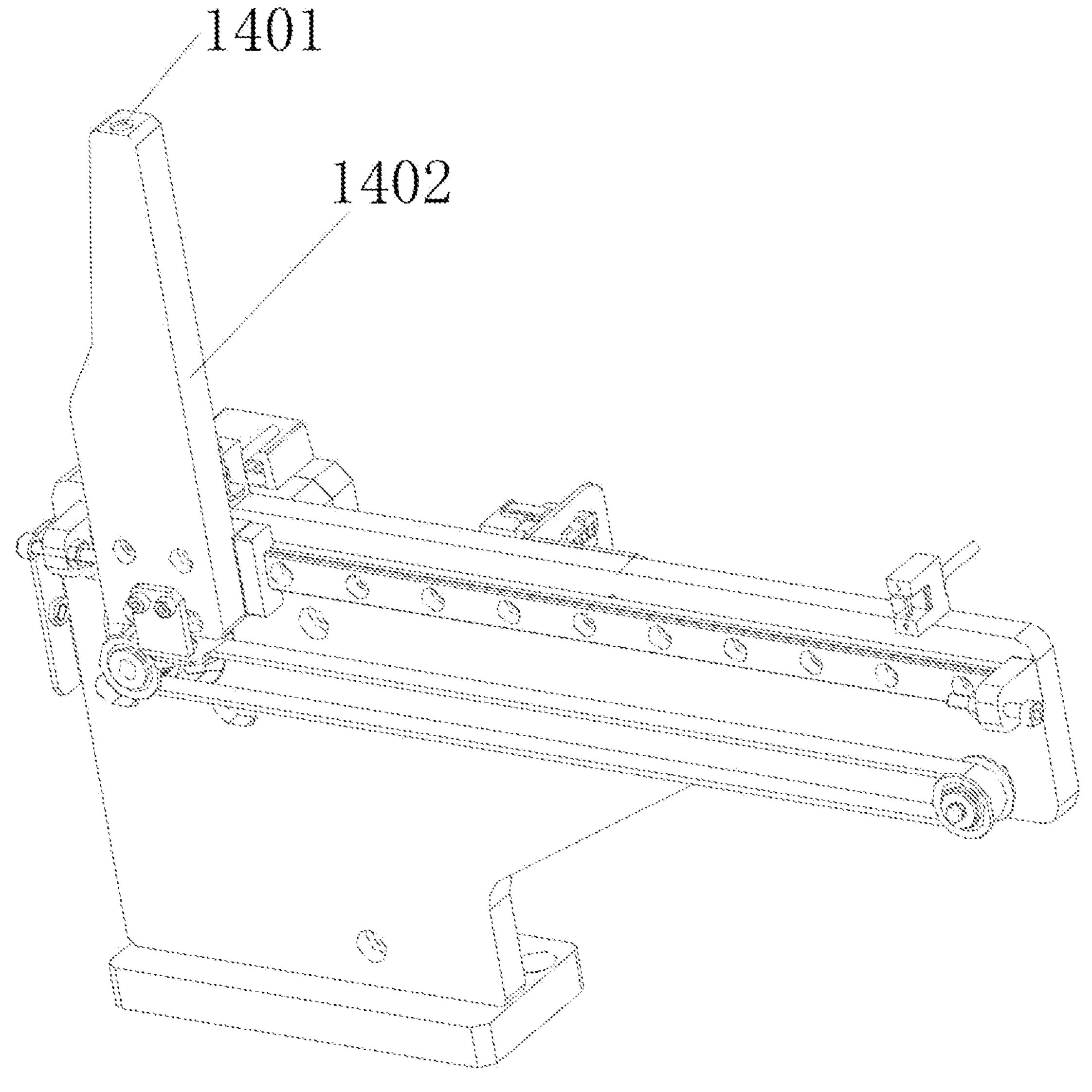
FIG. 10 is a schematic structural view of a PCR-tube transfer device.
Figure 11:
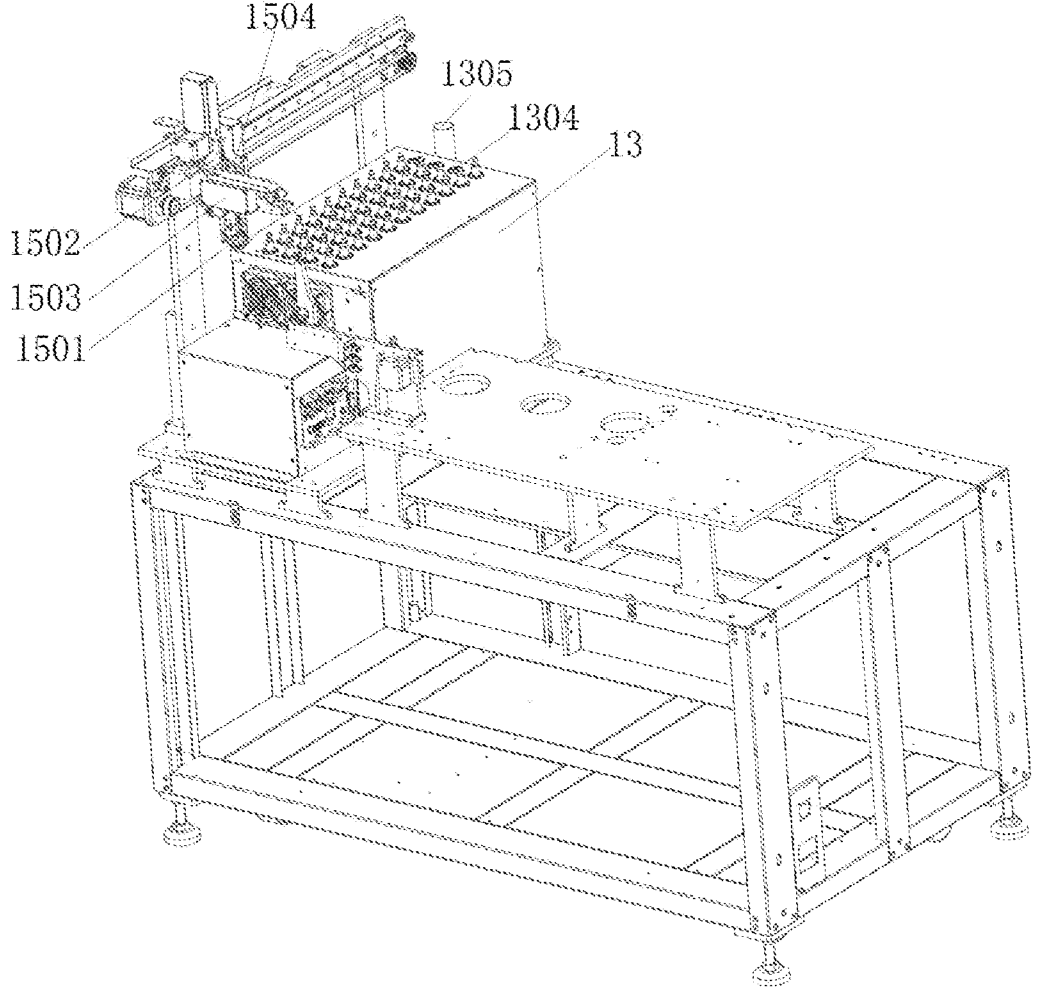
FIG. 11 is a schematic structural view of a PCR-tube transfer gripper.
Figure 12:
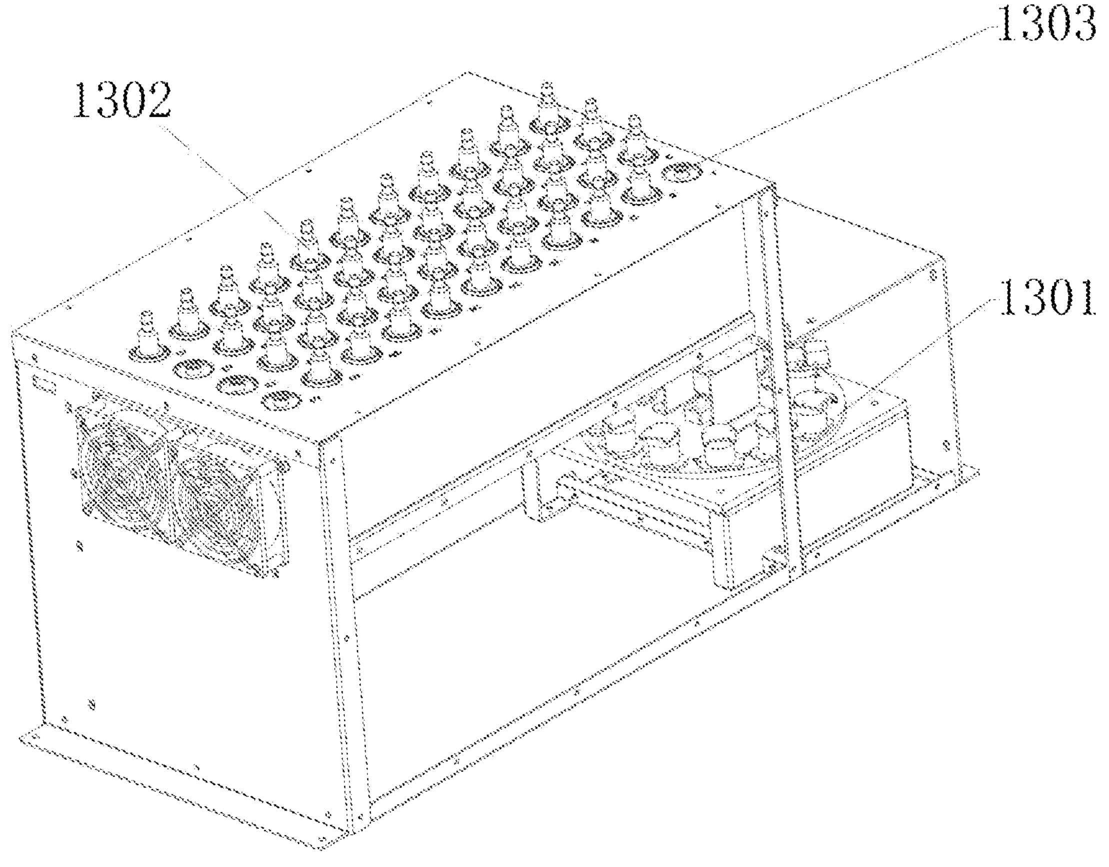
FIG. 12 is a schematic structural view of a fluorescent PCR test device.
Figure 13:
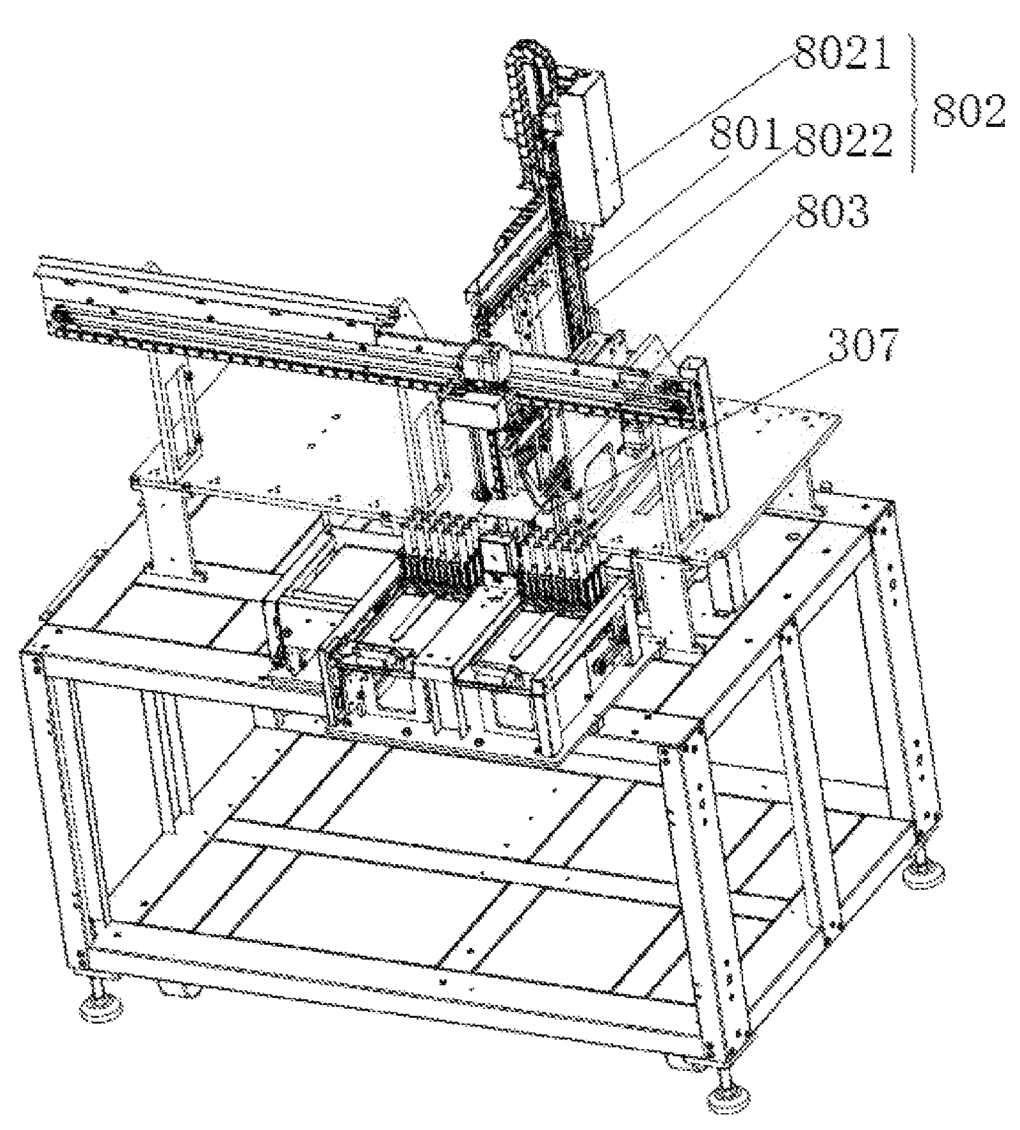
FIG. 13 is a schematic structural view of a filling device.
Figure 14:
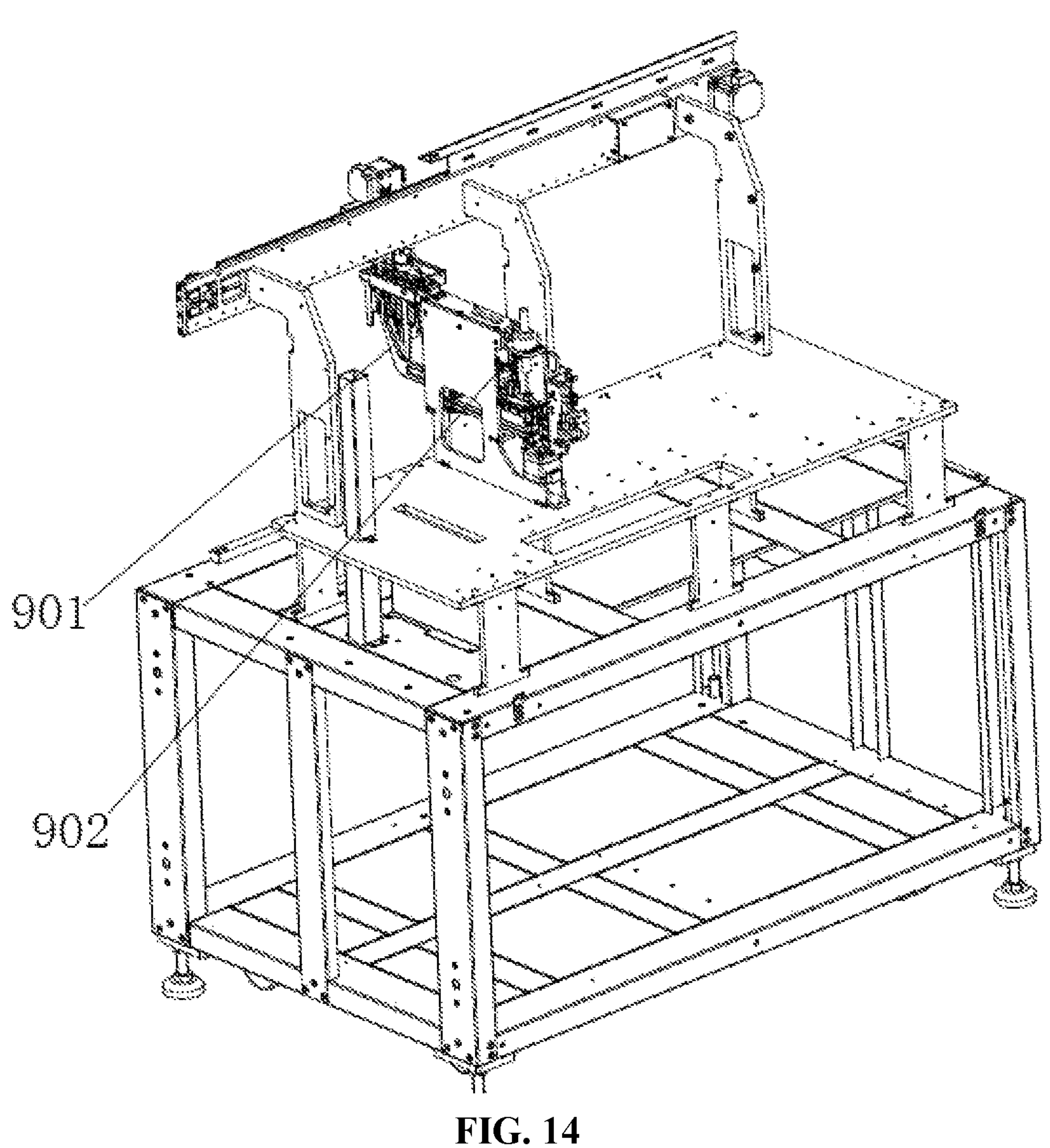
FIG. 14 is a schematic structural view of a low-temperature lysis device.
Figure 15:
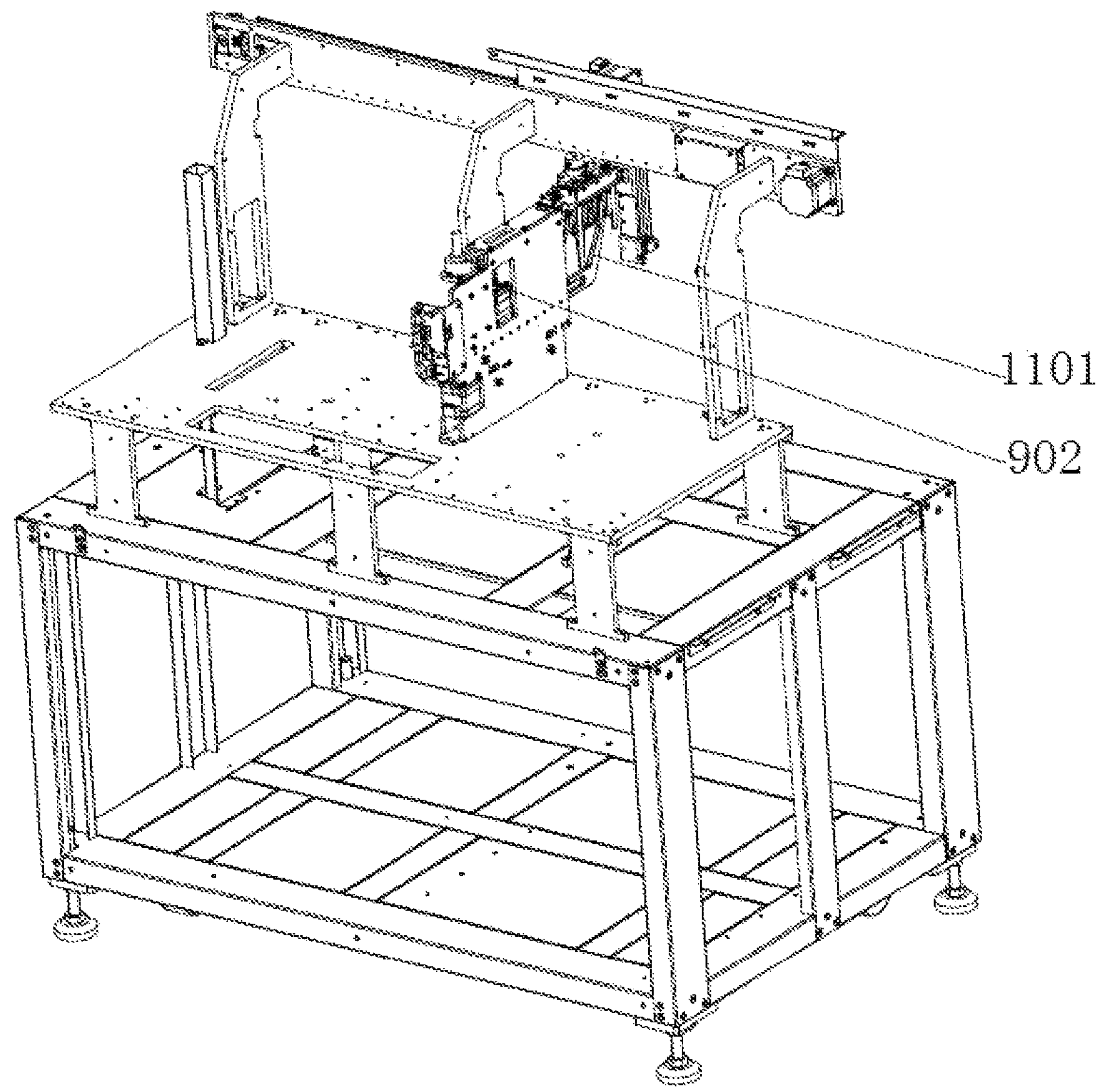
FIG. 15 is a schematic structural view of a high-temperature dissociation device.
Figure 16:
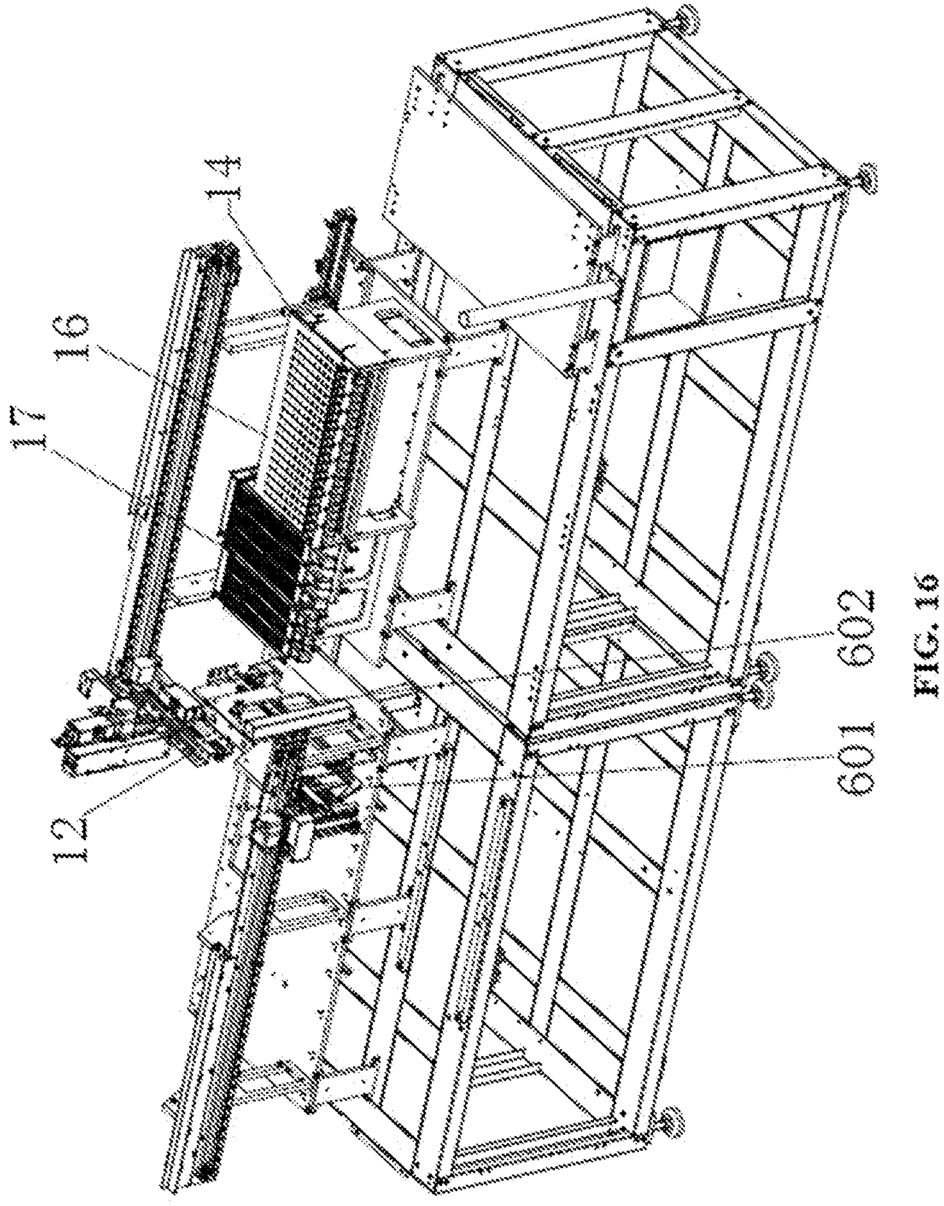
FIG. 16 is a schematic structural view of a refined-solution magnetic-absorption device.
Figure 17:
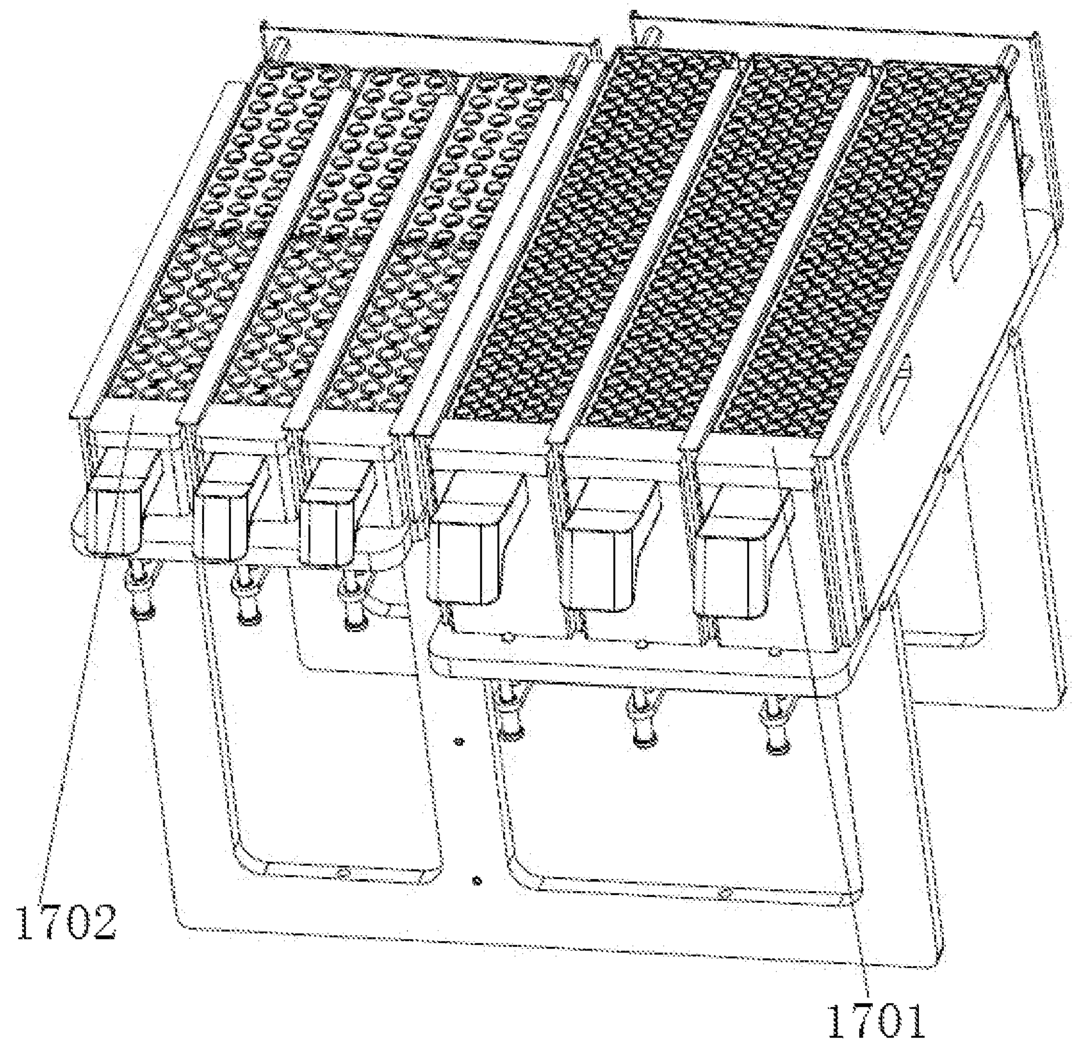
FIG. 17 is a schematic structural view of a consumable supply device.
Figure 18:
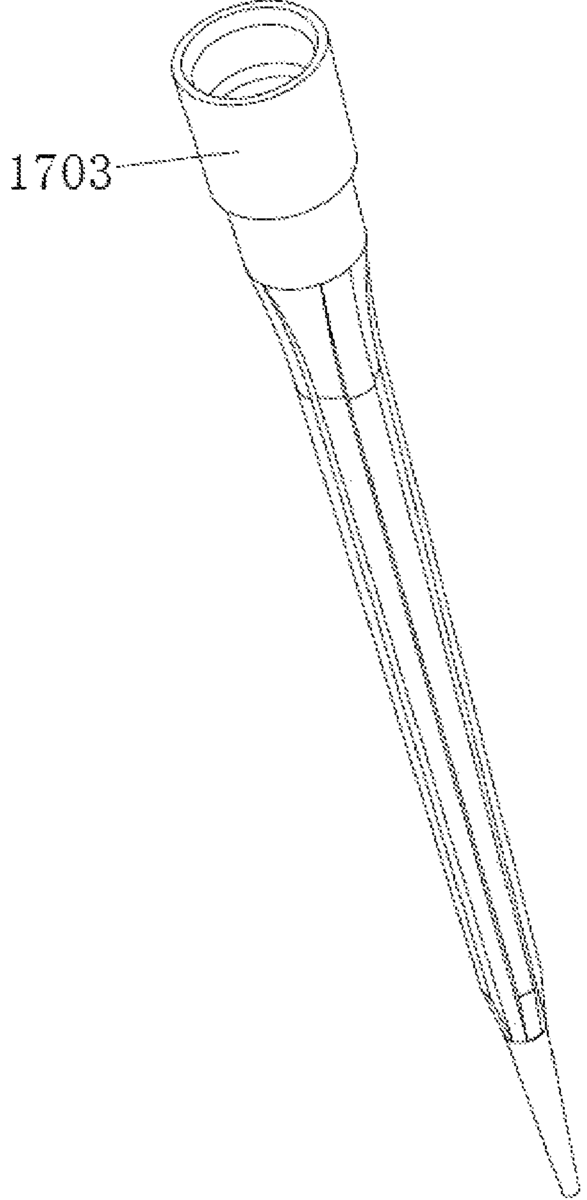
FIG. 18 is a schematic structural view of a TIP.
Figure 19:
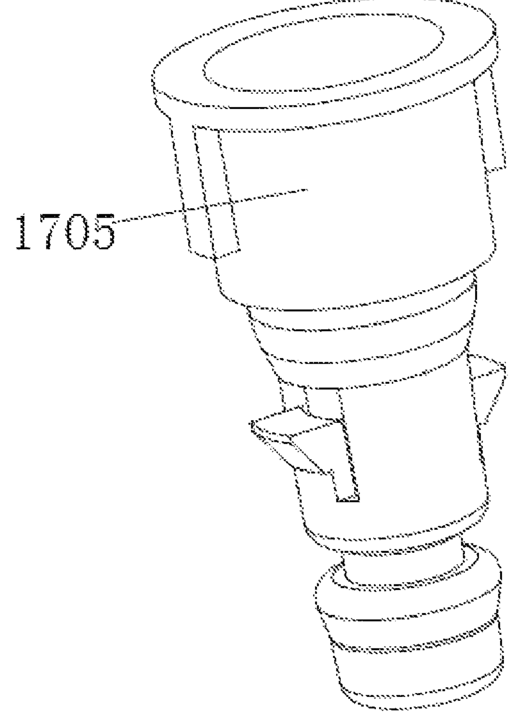
FIG. 19 is a schematic structural view of a PCR cover.
Figure 20:
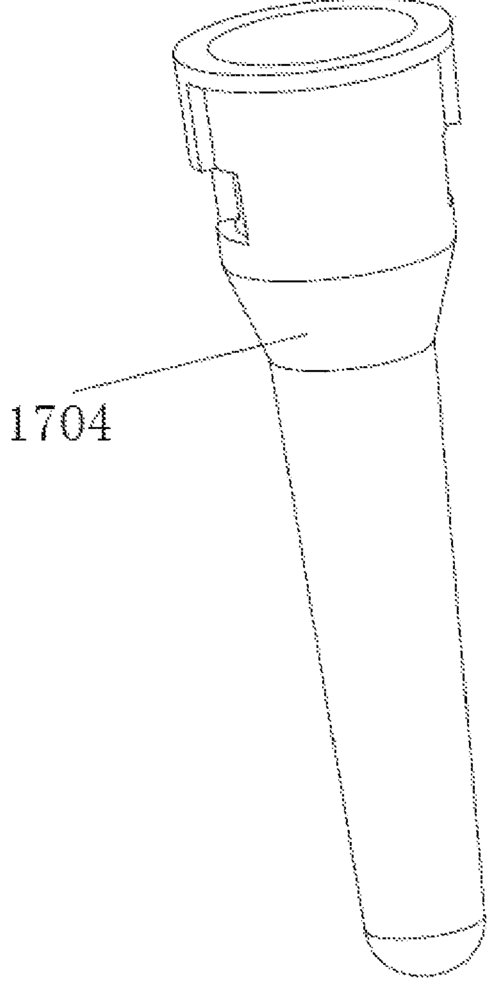
FIG. 20 is a schematic structural view of a PCR tube.
Figure 21:
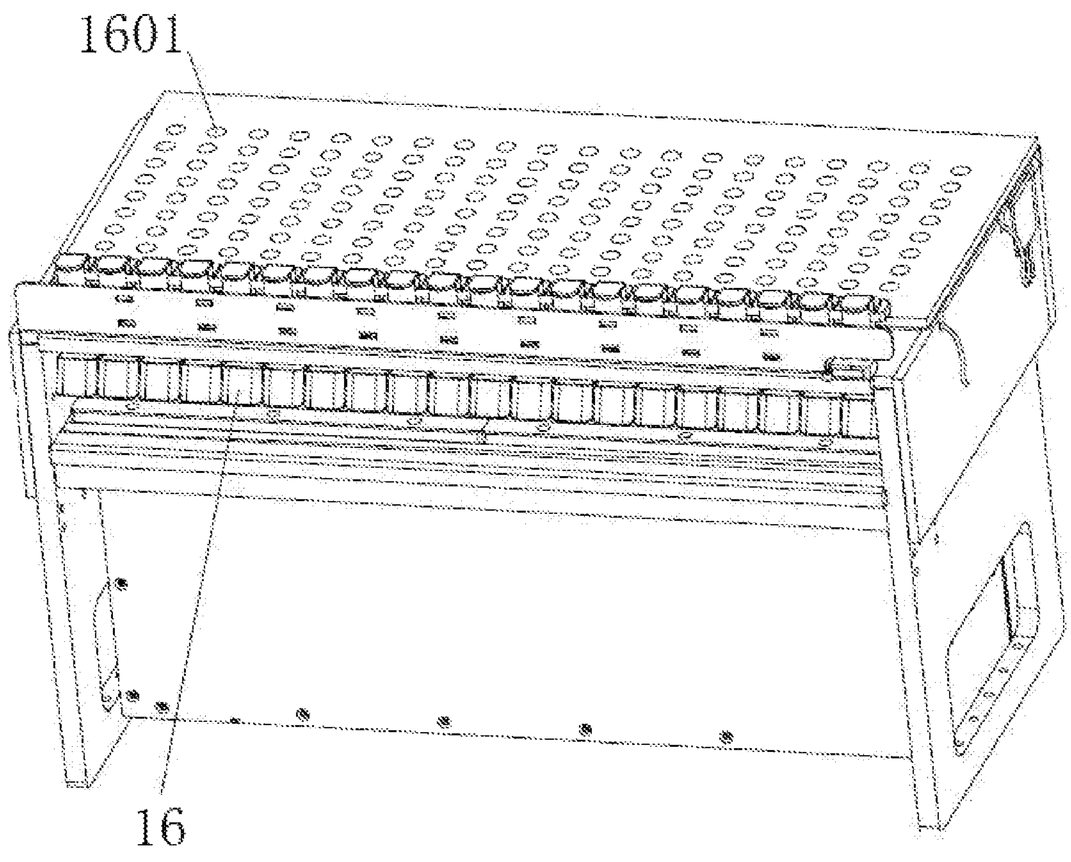
FIG. 21 is a schematic structural view of a refrigeration-reagent supply device.

It should be noted that a structure of the extraction strip 1 is as shown in FIG. 2, which has multiple reagent chambers for placing reagents and multiple empty chambers. The types of the reagents placed in the extraction strip 1 include a dissociation reagent 103, a detergent 105, a nucleic acid release solution 106, and a magnetic bead 107. The top of each reagent chamber is sealed with a film. Therefore, when addition is performed for the extraction strip 1, the film needs to be pierced in advance. An end of the extraction strip 1 is provided with a reaction chamber 109. A TIP 108 of 2 ml and a TIP 102 of 300 ul are placed in the extraction strip 1. Inner holes at the top of the above two TIPs can match a same TIP adapter. Moreover, two ends of the extraction strip 1 are each provided with a hanger 101. In addition, an identifiable identification 104 is provided on the extraction strip 1.

In the actual application process, structures, sizes, positions, and the like of the extraction-strip loading device 2, the sample-holder loading device 3, the extraction-strip transfer gripper 4, the nucleic-acid extraction device, the PCR test device, and the control device may be determined according to the actual situation and actual needs.

During using the nucleic acid extraction and fluorescent PCR test system according to the present application, first, the control device controls the extraction-strip loading device 2 to automatically load the extraction strip 1 and controls the sample-holder loading device 3 to load the sample to be tested, and then, the control device controls the nucleic-acid extraction device to operate to add the sample and the reagent required for the reaction into the extraction strip 1. The extraction strip 1 is moved, and the refining operations such as incubation and washing are performed on the sample and the reagent in the extraction strip 1, so as to obtain the nucleic acid refined solution. Finally, the PCR test device is used to perform fluorescent PCR tests on the nucleic acid, and the test results are fed back to the control device in real time. The position shift of the extraction strip 1 among the devices can be achieved by the extraction-strip transfer gripper 4, and the spatial movement of the extraction strip 1 can be achieved by controlling the extraction-strip transfer gripper 4, so that the extraction strip 1 can reach the required position for corresponding operation and reaction. In this way, the automatic operation of the nucleic acid extraction and test can be achieved, which is beneficial to lowering the intensity of manual operation and improving the test efficiency of the system.

The extraction-strip loading device 2 of the system has the function of on-line adding extraction strip 1, such that there is no need to immediately interrupt the on-going pushing and conveying of the previous extraction strip 1 every time a new extraction strip 1 is added, which is beneficial to improving the automation degree and the continuous conveying effect of the extraction-strip loading device 2, and is beneficial to improving the sample testing efficiency.

In summary, the nucleic acid extraction and fluorescent PCR test system according to the present application can effectively improve the flexibility and test efficiency of the nucleic acid extraction and test system, and make the sample test process more flexible and convenient.

Based on the above embodiments, preferably, the extraction-strip loading device 2 includes a passage and a pushing device which is configured to push the extraction strip 1 to move in the passage. One end of the passage is a gripping position 207 for the extraction strip 1. The pushing device is movable transversely, and the pushing device is connected to the control device.

Preferably, the passage may include a first passage 201 and a second passage 202 which is parallel and adjacent to the first passage 201, so that as many extraction strips 1 as possible can be placed therein. A first pushing device 203 is provided in the first passage 201, and a second pushing device 204 is provided in the second passage 202. The first pushing device 203 is configured to push the extraction strip 1 to move in the first passage 201, and the second pushing device 204 is configured to push the extraction strip 1 to move in the second passage 202. Moreover, a transfer device 205 is provided so as to transfer the extraction strip 1 from the first passage 201 to the second passage 202. The transfer device 205 may be arranged at another end of the first passage 201 and another end of the second passage 202. The first pushing device 203, the second pushing device 204 and the transfer device 205 are all connected to the control device.

Preferably, the first pushing device 203 and the second pushing device 204 are configured to move left and right and to move up and down, so that the extraction strip 1 can be placed more freely. In addition, the pushing device may not have the function of moving up and down. For example, a sensor may be provided, so that the sensor is triggered every time an extraction strip 1 is newly added, and the pushing device returns to an initial position for loading. The extraction-strip loading device 2 may be arranged in the front of the system, so as to facilitate the placement of the extraction strip 1. Any position of the first passage 201 and the second passage 202 may be used as a loading inlet 206 for the extraction strip 1.

For example, a left end of the second passage 202 is arranged as the grabbing position 207 for the extraction strip 1, and the transfer device 205 is arranged at a right end of the first passage 201 and a right end of the second passage 202.

In the actual application process, shapes, structures, sizes, positions, and the like of the extraction strip 1, the first passage 201, the second passage 202, the first pushing device 203, the second pushing device 204 and the transfer device 205 may be determined according to the actual situation and actual needs.

When the extraction-strip loading device 2 loads the extraction strip 1, first, the extraction strip 1 is loaded at the loading inlet 206 of the first passage 201, and then, the extraction strip 1 is pushed to move in the first passage 201 when the first pushing device 203 moves transversely. When the extraction strip 1 reaches the right end of the first passage 201, the extraction strip 1 can be transferred to the second passage 202 by the transfer device 205, and then the extraction strip 1 is conveyed from the right end to the left end of the second passage 202 by the second pushing device 204. When the extraction strip 1 reaches the grabbing position 207 of the second passage 202, the extraction-strip transfer gripper 4 can grip the extraction strip 1, so as to facilitate nucleic acid extraction of the extraction strip 1.

The movement, conveying and storage of the extraction strip 1 can be achieved in the first passage 201 and the second passage 202. In addition to the transverse movement, the first pushing device 203 and the second pushing device 204 of the device can also move up and down. Therefore, when a new extraction strip 1 is added in the first passage 201 or the second passage 202, the first pushing device 203 or the second pushing device 204 can continue pushing the extraction strip 1 transversely, without returning to the initial position immediately.

After the operation of adding the extraction strip 1 is completed, the first pushing device 203 or the second pushing device 204 is controlled to lower first to avoid collision with the extraction strip 1, and then the first pushing device 203 or the second pushing device 204 is moved to the initial position. When the newly added extraction strip 1 needs to be pushed again, the first pushing device 203 or the second pushing device 204 is controlled to rise to push the newly added extraction strip 1 again. Therefore, the device can achieve the on-line adding of the extraction strip 1, such that there is no need to immediately interrupt the on-going pushing and conveying every time a new extraction strip 1 is added, which is beneficial to improving the automation degree and use effect of the device.

Preferably, the gripping position 207 is provided with a jacking device 208 configured to move up and down to separate the extraction strip 1, and the jacking device 208 is connected to the control device.

It should be noted that, the jacking device 208 is provided at the grabbing position 207 so as to separate multiple huddled extraction strips 1. The extraction strip 1 which is jacked up by the jacking device 208 can be more conveniently and accurately grabbed by the extraction-strip transfer gripper 4.

It should be noted that, if the first pushing device 203 and the second pushing device 204 can move left and right and also up and down, an avoidance hole 209 for the first pushing device 203 and the second pushing device 204, which have been lowered, to pass may be defined in the extraction strip 1, so that the lowered first pushing device 203 and the lowered second pushing device 204 can smoothly avoid the extraction strip 1, so as to avoid hitting or knocking over the extraction strip 1.

Preferably, the sample-holder loading device 3 includes a sample holder 301 which is configured to load one or more samples, a loading pusher 302, an emergency pusher 303, a scanner 304, a transfer pusher 305 and an unloading pusher 306. The transfer pusher 305 is configured to transfer the sample to a scanning position of the scanner 304 and to move the sample after scanning to a sampling position 307, and the unloading pusher 306 is configured to convey the sample after sampling to a sample recovery area. The loading pusher 302, the emergency pusher 303, the scanner 304, the transfer pusher 305, and the unloading pusher 306 are all connected to the control device. The sample-holder loading device 3 may be arranged in the front of the system, so as to facilitate the placement of the sample holder 301. Multiple sample tubes 5 may be placed on the sample holder 301, and the sample tubes 5 are configured to contain sample solutions.

It should be noted that, the transfer pusher 305 can transfer the sample holder 301 loaded by the loading pusher 302 or the emergency pusher 303 to a barcode scanning position of the scanner 304. After the sample tubes 5 are scanned, the sample holder 301 is moved, so that the sample tubes 5 on the sample holder 301 are moved to the sampling position 307 sequentially, so as to help the subsequent filling device 8 to sample the sample tubes 5. Then, the sample holder 301 is moved to a return position. Finally, the sample holder 301 is pushed by the unloading pusher 306 to the sample recovery area. When some samples need to be tested urgently, these samples can be put into the emergency pusher 303 for being tested as early as possible. When there is a new sample to be tested, the sample to be tested can be placed on the sample-holder loading device for test instantly, without waiting for the completion of test of the whole last batch of preset samples, so as to improve the sample testing efficiency and the use flexibility.

In the actual application process, shapes, structures, sizes, materials, positions, and the like of the sample holder 301, the sample tubes 5, the loading pusher 302, the emergency pusher 303, the scanner 304, the transfer pusher 305 and the unloading pusher 306 may be determined according to the actual situation and actual needs.

Based on the above embodiments, preferably, the extraction-strip transfer gripper 4 includes an openable gripper device 401 which is configured to grip the extraction strip 1, a gripper lifting device 402 which is configured to drive the gripper device 401 to move up and down, and a gripper transverse-movement device 403 which is configured to drive the gripper lifting device 402 to move transversely. The gripper device 401 is arranged on the gripper lifting device 402, and the gripper lifting device 402 is slidably connected with the gripper transverse-movement device 403. The gripper device 401, the gripper lifting device 402 and the gripper transverse-movement device 403 are all connected to the control device. Therefore, the extraction strip 1 can be effectively gripped and the extraction strip 1 can be driven to move by controlling the opening and closing of the gripper device 401 and the spatial movement of the gripper device 401, so that the extraction strip 1 can reach the required position for corresponding operation.

It should be noted that, the extraction-strip transfer gripper 4 may be arranged in front of the sealing-film piercing device 7, the filling device 8, the low-temperature lysis device 9, the magnetic-bead washing device 10, the high-temperature dissociation device 11, the refined-solution magnetic-absorption device 6 and the discard device 18. The extraction-strip transfer gripper 4 grips the extraction strip 1 from the gripping position for the extraction strip 1 on the extraction-strip loading device 2. After the extraction strip 1 is gripped successfully, the extraction strip 1 is transferred to the front of the sealing-film piercing device 7, so as to facilitate the operation of piercing through the sealing film.

In the actual application process, shapes, structures, sizes, positions, and the like of the gripper device 401, the gripper lifting device 402 and the gripper transverse-movement device 403 may be determined according to the actual situation and actual needs.

Based on the above embodiments, preferably, the nucleic-acid extraction device includes a sealing-film piercing device 7 which is configured to pierce through a sealing film of the extraction strip 1, a filling device 8 which is configured to add the sample to be tested to the extraction strip 1, a reagent needle 12, a magnetic-bead washing device 10, a high-temperature dissociation device 11 which is configured to perform high-temperature incubation on the sample, and a refined-solution magnetic-absorption device 6 which is configured to perform magnetic absorption refinement on the sample to obtain a nucleic acid refined solution. The reagent needle 12 is configured to add a corresponding reagent into the extraction strip 1 or a PCR tube 1704 and to add the nucleic acid refined solution of the extraction strip 1 into the PCR tube 1704. In addition, the reagent needle 12 can further be used to obtain a PCR cover 1705, snap the PCR cover 1705 onto the PCR tube 1704, and transfer the capped PCR tube 1704.

Preferably, the sealing-film piercing device 7 includes a piercer 701 and a driving assembly. The driving assembly is connected with the piercer 701 to drive the piercer 701 to move. When the piercer 701 moves to a piercing position, the piercer 701 pierces through the sealing film of the extraction strip 1. The driving assembly is connected to the control device. Therefore, the sealing film of the extraction strip 1 is pierced through by the piercer 701, which effectively solves the problem of piercing through the sealing film at the top of the extraction strip 1 before using the reagent in the extraction strip 1.

In addition, the sealing-film piercing device 7 further includes a washing device 702 which is connected to the control device. The washing device 702 is configured to wash the piercer 701 when the piercer 701 moves to a washing position. The piercer 701 is cleaned by using the washing device 702, so that the piercer 701 can be reused, thus effectively reducing the use of consumables and reducing the cost of users. In addition, the sealing-film piercing device 7 has a simple structure, is safe and reliable, has a low risk of system pollution, and is convenient to maintain.

It should be noted that, the sealing-film piercing device 7 may be arranged close to the refrigeration-reagent supply device 16, so as to facilitate the subsequent addition of refrigeration reagent. The sealing-film piercing device 7 may be provided with a piercing forward-backward pusher 703 which is used to cooperate with the extraction-strip transfer gripper 4, so as to achieve the three-dimensional spatial movement of the extraction strip 1. Therefore, the piercing forward-backward pusher 703 can push the extraction strip 1 from the extraction-strip transfer gripper 4 into the sealing-film piercing device 7, and then push the extraction strip 1 back to the extraction-strip transfer gripper 4 after the piercing is completed, and then the extraction-strip transfer gripper 4 transfers the extraction strip 1 to the front of the filling device 8.

The sealing-film piercing device 7 may be provided with a scanner 704, so as to identify the identification 104 on the extraction strip 1. After the sealing film of the extraction strip 1 is pierced through, the reagent needle 12 obtains a TIP 1703 from the consumable supply device 17, then draws the relevant reagents for the reaction from the refrigeration-reagent supply device 16 and adds the reagents into the reaction chamber 109 of the extraction strip 1, and finally, the reagent needle 12 discards the used TIP 1703, so as to facilitate the next operation.

In the actual application process, shapes, structures, sizes, positions and the like of the piercing device, the washing device 702, the piercing forward-backward pusher 703 and the scanner may be determined according to the actual situation and actual needs.

Preferably, the filling device 8 includes a sample needle 801 which is configured to draw the sample and a sample moving device 802 which is configured to drive the sample needle 801 to move in space. The sample needle 801 is connected to the sample moving device 802, and the sample moving device 802 is connected to the control device.

It should be noted that, the sample moving device 802 may include a sample forward-backward movement manipulator 8022 which is configured to drive the sample needle 801 to move forward and backward, and a sample vertical movement manipulator 8021 which is configured to drive the sample needle 801 to move up and down. In addition, a first forward-backward pusher 803 may be provided, which is configured to cooperate with the extraction-strip transfer gripper 4, so as to achieve the three-dimensional spatial movement of the extraction strip 1 and ensure that the extraction strip 1 can be moved to a filling position of the filling device 8. Therefore, the first forward-backward pusher can push the extraction strip 1 from the extraction-strip transfer gripper 4 into the filling device 8, and then push the extraction strip 1 back to the extraction-strip transfer gripper 4 after the filling is completed, and then the extraction-strip transfer gripper 4 transfers the extraction strip 1 to the front of the low-temperature lysis device 9.

In addition, it should be noted that, the bottom of the sample needle 801 is provided in a vertical direction with a TIP adapter which is configured to obtain the TIP 108 of 2 ml in the extraction strip 1. When the first forward-backward pusher pushes the extraction strip 1 into the filling device 8, the sample needle 801 can obtain the TIP 108 of 2 ml in the extraction strip 1, the sample needle 801 moves forward to above the sampling position 307 of the sample-holder loading device 3, and then the sample moving device 802 drives the sample needle 801 to move to draw the sample to be tested and add the sample into the reaction chamber 109 of the extraction strip 1. Then, the sample needle 801 draws the required reagents from reagent holes in the extraction strip 1, and adds the required reagents into the reaction chamber 109. The required reagents include a magnetic bead 107 and a nucleic acid release solution 106 which are required by the reaction. Then, the liquids in the reaction chamber 109 are mixed uniformly by a draw-expel method, so as to complete the filling. Finally, the sample needle 801 returns the TIP 108 of 2 ml onto the extraction strip 1.

In the actual application process, shapes, structures, sizes, positions and the like of the sample needle 801 and the sample moving device 802 may be determined according to the actual situation and actual needs.

It should be noted that, the nucleic-acid extraction device may further include a low-temperature lysis device 9. The low-temperature incubation is beneficial to the combination of the nucleic acid and the magnetic bead 107. The sample solution generally needs to go through the low-temperature incubation of the low-temperature lysis device 9 first, and then the magnetic bead 107 is washed by the magnetic-bead washing device 10, so as to remove other substances other than the combination of the nucleic acid and the magnetic bead 107. Then, the sample solution goes through the high-temperature incubation of the high-temperature dissociation device 11. The high-temperature incubation is beneficial to the separation of the nucleic acid from the magnetic bead 107. However, due to different nucleic acid release solutions 106, the sample solution may sometimes not need to go through the low-temperature incubation of the low-temperature lysis device 9. In this case, the extraction-strip transfer gripper 4 can be controlled to transfer the extraction strip 1 from the filling device 8 directly to the front of the magnetic-bead washing device 10, rather than to the low-temperature lysis device 9.

Preferably, the high-temperature dissociation device 11 includes an incubation heating block 902 which is configured to heat the reaction chamber 109 of the extraction strip 1, and the incubation heating block 902 is connected to the control device.

It should be noted that, a heating block driving device which is connected to the incubation heating block 902 may be provided, and the heating block driving device is connected to the control device. The heating block driving device is configured to drive the incubation heating block 902 to move in space, so that the heating block can approach or move away from the reaction chamber 109.

It should be noted that, the low-temperature lysis device 9 has a structure similar to the high-temperature dissociation device 11, the main difference is that a heating temperature of the incubation heating block 902 is different. The heating temperature of the low-temperature lysis device 9 is lower, and the heating temperature of the high-temperature dissociation device 11 is higher. When the incubation needs to be performed on the reaction chamber 109, the heating block driving device is controlled to operate to drive the incubation heating block 902 to approach the reaction chamber 109 to heat the reaction chamber 109. After the incubation is completed, the incubation heating block 902 is controlled to separate from the reaction chamber 109. During the heating of the incubation heating block 902, the sample solution releases the nucleic acid under the action of the nucleic acid release solution 106, and the nucleic acid attaches to the magnetic bead 107.

In addition, it should be noted that, the low-temperature lysis device 9 may be provided with a second forward-backward pusher 901 which is configured to cooperate with the extraction-strip transfer gripper 4, so as to achieve the three-dimensional spatial movement of the extraction strip 1. Therefore, the second forward-backward pusher 901 can push the extraction strip 1 from the extraction-strip transfer gripper 4 into the low-temperature lysis device 9, and then push the extraction strip 1 back to the extraction-strip transfer gripper 4 after the low-temperature incubation is completed, and the extraction-strip transfer gripper 4 can then transfer the extraction strip 1 to the front of the magnetic-bead washing device 10.

Preferably, the magnetic-bead washing device 10 includes a detergent needle 1001, a detergent driving device 1002 which is configured to drive the detergent needle 1001 to move in space, a magnet device 1003 which is configured to selectively apply a magnetic field to the reaction chamber 109 of the extraction strip 1, and a magnet driving device which is configured to drive the magnet device 1003 to rotate. The magnet driving device is connected to the magnet device 1003, and the detergent needle 1001 is connected to the detergent driving device 1002. The magnet driving device and the detergent driving device 1002 are both connected to the control device.

It should be noted that, the magnetic-bead washing device 10 may be provided with a fourth forward-backward pusher 1004 which is configured to cooperate with the extraction-strip transfer gripper 4, so as to achieve the three-dimensional spatial movement of the extraction strip 1. Therefore, the fourth forward-backward pusher 1004 can push the extraction strip 1 from the extraction-strip transfer gripper 4 into the magnetic-bead washing device 10 for magnetic absorption. In addition, the detergent needle 1001 is provided in a vertical direction with a TIP adapter which is configured to obtain the TIP 108 of 2 ml in the extraction strip 1.

During the magnetic absorption, first, the TIP 108 of 2 ml in the extraction strip 1 is aligned with the detergent needle 1001, and the detergent needle 1001 moves downward to obtain the TIP 108 of 2 ml. Then, the extraction strip 1 is moved to a magnetic absorption position, and one of a first magnet and a second magnet is rotated to the magnetic absorption position by rotating the magnet device 1003, so that the magnetic bead 107 attached with the nucleic acid in the reaction chamber 109 of the extraction strip 1 is accumulated on a side wall of the reaction chamber 109 under the magnetic force. During magnetic absorption, the reaction chamber 109 of the extraction strip 1 is located below the detergent needle 1001. The detergent needle 1001 moves downward to draw away the liquid in the reaction chamber 109, and the magnetic bead 107 is retained on the inner wall of the reaction chamber 109 under the magnetic force. Then, the magnet is rotated to leave the magnetic absorption position and avoid the movement space of the extraction strip 1. After that, the empty chamber in the extraction strip 1 is aligned with the detergent needle 1001 by pushing the extraction strip 1, and the detergent needle 1001 expels out the liquid drawn from the TIP 108 of 2 ml. The reagent chamber in the extraction strip 1, for placing the detergent 105, is aligned with the detergent needle 1001 by pushing the extraction strip 1, and the detergent needle 1001 draws the detergent 105. The reaction chamber 109 in the extraction strip 1 is aligned with the detergent needle 1001 by pushing the extraction strip 1, and the detergent needle 1001 adds the detergent 105 drawn from the TIP 108 of 2 ml into the reaction chamber 109, and mixes the magnetic bead 107 with the detergent 105 in the reaction chamber 109 uniformly by a draw-expel method. Then, one of the first magnet and the second magnet is rotated to the magnetic absorption position, so that the magnetic bead 107 attached with the nucleic acid in the reaction chamber 109 of the extraction strip 1 is accumulated on the side wall of the reaction chamber 109 under the magnetic force. The detergent needle 1001 moves downward to draw away the liquid in the reaction chamber 109, and the magnetic bead 107 is retained on the inner wall of the reaction chamber 109 under the magnetic force. Then, the magnet is rotated to leave the magnetic absorption position and avoid the movement space of the extraction strip 1. Then, the empty chamber in the extraction strip 1 is aligned with the detergent needle 1001 by pushing the extraction strip 1, and the detergent needle 1001 expels out the liquid drawn from the TIP 108 of 2 ml. After that, the magnetic bead 107 can be washed several times according to the requirements of the test items. The waste liquid after washing is expelled into the empty chamber in the extraction strip 1, and the magnetic bead 107 after washing is retained in the reaction chamber 109. After the washing of the magnetic bead 107 is completed, the placement position of the TIP 108 of 2 ml in the extraction strip 1 is aligned with the detergent needle 1001 by pushing the extraction strip 1, and the detergent needle 1001 returns the TIP 108 of 2 ml onto the extraction strip 1. Then, the placement position of the TIP 102 of 300 ul in the extraction strip 1 is aligned with the detergent needle 1001 by pushing the extraction strip 1, and the detergent needle 1001 moves downward to obtain the TIP 102 of 300 ul. Then, the dissociation reagent 103 in the extraction strip 1 is aligned with the detergent needle 1001 by pushing the extraction strip 1, and the detergent needle 1001 draws the dissociation reagent 103. The dissociation reagent 103 is used to separate the nucleic acid attached to the magnetic bead 107 from the magnetic bead 107. Then, the reaction chamber 109 in the extraction strip 1 is aligned with the detergent needle 1001 by pushing the extraction strip 1, and the detergent needle 1001 adds the dissociation reagent 103 drawn from the TIP 102 of 300 ul into the reaction chamber 109 and mixes the liquids in the reaction chamber 109 uniformly by a draw-expel method. Then, the placement position of the TIP 102 of 300 ul in the extraction strip 1 is aligned with the detergent needle 1001 by pushing the extraction strip 1, and the detergent needle 1001 returns the TIP 102 of 300 ul into the extraction strip 1, thus completing the whole magnetic absorption.

After the magnetic absorption is completed, the fourth forward-backward pusher 1004 pushes the extraction strip 1 back to the extraction-strip transfer gripper 4, and the extraction-strip transfer gripper 4 transfers the extraction strip 1 to the front of the high-temperature dissociation device 11.

Preferably, the high-temperature dissociation device 11 may be provided with a third forward-backward pusher 1101 which is configured to cooperate with the extraction-strip transfer gripper 4, so as to achieve the three-dimensional spatial movement of the extraction strip 1. Therefore, the third forward-backward pusher 1101 can push the extraction strip 1 from the extraction-strip transfer gripper 4 into the high-temperature dissociation device 11 for high-temperature incubation. Under the action of the dissociation reagent 103, the nucleic acid attached to the magnetic bead 107 can be separated from the magnetic bead 107 after a certain period of high-temperature incubation. After the high-temperature incubation is completed, the extraction strip 1 is pushed back to the extraction-strip transfer gripper 4, and the extraction-strip transfer gripper 4 then transfers the extraction strip 1 to the front of the refined-solution magnetic-absorption device 6.

Preferably, the refined-solution magnetic-absorption device 6 may be arranged within a movement range of the reagent needle 12, so as to help the reagent needle 12 to draw the refined solution in the reaction chamber 109 of the extraction strip 1. The refined-solution magnetic-absorption device 6 may be provided with a refinement forward-backward pusher 601 and a magnet 602. The refinement forward-backward pusher 601 is configured to cooperate with the extraction-strip transfer gripper 4, so as to achieve the three-dimensional spatial movement of the extraction strip 1. Therefore, the refinement forward-backward pusher 601 can push the extraction strip 1 from the extraction-strip transfer gripper 4 into the refined-solution magnetic-absorption device 6 for refinement. After the refinement is completed, the extraction strip 1 is pushed back to the extraction-strip transfer gripper 4, and the extraction-strip transfer gripper 4 then transfers the extraction strip 1 to the front of the discard device 18. The magnet 602 is configured to apply magnetic force to the reaction chamber 109 of the extraction strip 1, so that the magnetic bead 107 in the reaction chamber 109 is accumulated on the side wall of the reaction chamber 109 under the magnetic force, and the nucleic acid is retained in the liquid, thus obtaining the nucleic acid refined solution required for test.

Based on the above embodiments, preferably, the nucleic acid extraction and fluorescent PCR test system further includes a refrigeration-reagent supply device 16 which has a refrigeration function and is configured to provide different reagents.

It should be noted that, the refrigeration-reagent supply device 16 has the refrigeration function to better reserve the reagent that needs to be refrigerated. Moreover, a liquid draw hole 1601 is defined at the top of the refrigeration-reagent supply device 16. The liquid draw hole 1601 is matched with the reagent needle 12 in size, so that the reagent needle 12 can easily draw the reagent.

Preferably, the system may include a consumable supply device 17 which is configured to provide TIPs 1703, PCR-tubes 1704 and PCR covers 1705. The consumable supply device 17 is provided with a TIP consumable holder 1701 which is configured to hold the TIPs 1703, and a PCR consumable holder 1702 which is configured to hold the PCR-tubes 1704 and the PCR covers 1705.

Preferably, each of the TIPs 1703 and the PCR covers 1705 is provided with an inner hole at the top thereof, and the inner hole is matched with the reagent needle 12 in size, so that the reagent needle 12 can easily take the TIPs 1703 and the PCR covers 1705. Moreover, the inner holes at the top of the TIPs 1703 and the PCR covers 1705 may be matched with a TIP adapter hole of the reagent needle 12, so that the reagent needle 12 can easily take the TIPs 1703 and the PCR covers 1705.

In addition, it should be further noted that, the reagent needle 12 can achieve the three-dimensional spatial movement by using the structure including a horizontal movement manipulator, a forward-backward movement manipulator, and a vertical movement manipulator. The reagent needle 12 may be provided with a TIP adapter in the vertical direction. The TIP adapter is configured to obtain the TIP 1703 or the PCR cover 1705. The movement range of the reagent needle 12 covers the refined-solution magnetic-absorption device 6, the sealing-film piercing device 7, the consumable supply device 17 and the refrigeration-reagent supply device 16. After obtaining the TIP 1703, the reagent needle 12 can add the reagent in the refrigeration-reagent supply device 16 into the reaction chamber 109 of the extraction strip 1 or the PCR tube 1704, and add the nucleic acid refined solution of the reaction chamber 109 into the PCR tube 1704, and then can obtain the PCR cover 1705 to snap the PCR cover 1705 onto the PCR tube 1704 for sealing, and then can transfer the sealed PCR tube 1704 to a PCR-tube transfer device 14.

For example, the reagent needle 12 can obtain the TIP 1703 from the consumable supply device 17, draw the nucleic acid refined solution from the reaction chamber 109 of the extraction strip 1, then add the nucleic acid refined solution into the PCR tube 1704 on the consumable supply device 17, and discard the TIP 1703 from a TIP discard port. After obtaining the TIP 1703 from the consumable supply device 17, the reagent needle 12 draws the reagent required for reaction from the refrigeration-reagent supply device 16 and adds the reagent into the same PCR tube 1704, and then discards the TIP 1703 from the TIP discard port. Then, the reagent needle 12 obtains the PCR cover 1705 from the consumable supply device 17, and snaps the PCR cover 1705 onto the PCR tube 1704 in which the nucleic acid refined solution and the reagent have already been added. Finally, the reagent needle 12 transfers the sealed PCR-tube.

Preferably, the reagent needle 12 may include a needle device 1201 and a needle driving device which is configured to drive the needle device 1201 to move in space. The needle device 1201 and the needle driving device are both connected to the control device. The needle driving device may include a needle horizontal movement manipulator 12021 which is configured to drive the needle device 1201 to move horizontally, a needle forward-backward movement manipulator 12022 which is configured to drive the needle device 1201 to move forward and backward, and a needle vertical movement manipulator 12023 which is configured to drive the needle device 1201 to move vertically, so as to achieve the three-dimensional spatial movement of the needle device 1201.

Based on the above embodiments, preferably, the nucleic acid extraction and fluorescent PCR test system further includes a discard device 18 which is configured to recycle the discarded extraction strip 1. The discard device 18 is connected to the control device.

Preferably, the discard device 18 may include a waste liquid needle 1801 which is configured to draw a waste liquid from the extraction strip 1, an openable gripper 1802 which is configured to grip the discarded extraction strip 1, an opening-closing driving device which is configured to drive the openable gripper 1802 to open or close, and a lifting driving device which is configured to drive the waste liquid needle 1801 to move up and down. The opening-closing driving device and the lifting driving device are both connected to the control device.

It should be noted that after the reagent needle 12 adds the nucleic acid refined solution of the extraction strip 1 into the PCR tube 1704, the extraction strip 1 can be discarded. The discard device 18 may be provided with a fifth forward-backward pusher 1803. The fifth forward-backward pusher 1803 is configured to cooperate with the extraction-strip transfer gripper 4, so as to achieve the three-dimensional spatial movement of the extraction strip 1. Therefore, the fifth forward-backward pusher 1803 can push the extraction strip 1 from the extraction-strip transfer gripper 4 into the discard device 18, then the reaction chamber 109 and the reagent chambers in the extraction strip 1 are sequentially pushed to below the waste liquid needle 1801. The waste liquid needle 1801 can move vertically, so as to draw the remaining liquid from the reaction chamber 109 and the reagent chambers. After the liquid drawing is completed, the fifth forward-backward pusher 1803 pushes the extraction strip 1 to a discard position of the openable gripper 1802. Finally, the openable gripper 1802 opens to discard the extraction strip 1 at the discard position.

Based on the above embodiments, preferably, the PCR test device includes a fluorescent PCR test device 13 which is configured to perform various fluorescent PCR tests on the sealed PCR tube 1704. The fluorescent PCR test device 13 is connected to the control device.

Preferably, the PCR test device further includes a PCR-tube transfer device 14 and a PCR-tube transfer gripper 15. The PCR-tube transfer device 14 and the PCR-tube transfer gripper 15 are both connected to the control device. The PCR-tube transfer device 14 is configured to transfer the sealed PCR tube 1704 to a gripping position of the PCR-tube transfer gripper 15. The PCR-tube transfer gripper 15 is configured to transfer the PCR tube 1704 from the PCR-tube transfer device 14 to the fluorescent PCR test device 13.

It should be noted that the reagent needle 12 can transfer the sealed PCR tube to the PCR-tube transfer device 14. The PCR-tube transfer device 14 is provided with a transfer block 1402 which is movable horizontally. The PCR tube 1704 may be arranged in a PCR-tube placement hole 1401 at the top of the transfer block 1402, and then the PCR tube 1704 is transferred to the gripping position of the PCR-tube transfer gripper 15.

Preferably, the fluorescent PCR test device 13 includes a housing, a photometry assembly 1301 and temperature control components. The housing is provided with multiple test positions 1303 for placing the PCR tube 1704, and each of the multiple test positions 1303 is provided with the corresponding temperature control component, so that the temperatures in the multiple test positions 1303 are independently controlled to rise or fall. The photometry assembly 1301 and the temperature control components are both connected to the control device. The photometry assembly 1301 includes a light source assembly which is configured to provide a test light source and a driving component which is configured to drive the light source assembly to move. The number of the light source assembly is plural. The multiple light source assemblies provide different types of light sources, and each light source assembly illuminates, driven by the driving component, the corresponding test position 1303.

It should be noted that the fluorescent PCR test device 13 may include a pressing cylinder 1302 which is configured to press the PCR tube 1704 tightly. The housing is provided with a magnetic attraction component, and the pressing cylinder 1302 is provided with a magnet member, so that the pressing cylinder 1302 is attracted to the housing, thus pressing the PCR tube tightly. Since each test position 1303 is provided with the corresponding temperature control component which is configured to control the temperature of the PCR tube 1704, each test position 1303 can independently control the temperature to rise or fall, thus achieving simultaneous on-line test of different test items.

It should be further noted that the photometry assembly 1301 and the temperature control components are both connected to the control device, so that the fluorescent PCR test device 13 can perform real-time fluorescence test while the temperature rises or falls. Moreover, each test position 1303 is provided with the independent pressing cylinder 1302. The pressing cylinder 1302 has the function of pressing the PCR tube 1704 tightly. The pressing cylinder 1302 achieves rapid mounting and fixation by the magnetic attraction, and ensures the tight fit between the PCR tube 1704 and the temperature control component, so as to improve the test effect.

In addition, it should be noted that, the PCR-tube transfer gripper 15 is movable in three-dimensional space, and is configured to grip the sealed PCR tube 1704 or the pressing cylinder 1302, so as to facilitate the subsequent test by the fluorescent PCR test device 13. The PCR-tube transfer gripper 15 may include a PCR gripper 1501 which is configured to grip the sealed PCR tube 1704 and the pressing cylinder 1302, a PCR horizontal movement manipulator 1502 which is configured to drive the PCR gripper 1501 to move horizontally, a PCR forward-backward movement manipulator 1503 which is configured to drive the PCR gripper 1501 to move forward and backward, and a PCR vertical movement manipulator 1504 which is configured to drive the PCR gripper 1501 to move vertically. The PCR gripper 1501 can grip the pressing cylinder 1302 on the fluorescent PCR test device 13, place the pressing cylinder 1302 on a pressing cylinder placement position 1304, grip the PCR tube 1704 from the PCR-tube transfer device 14 to place the PCR tube 1704 on the test position 1303 of the fluorescent PCR test device 13 with the pressing cylinder 1302 being removed, and then grip the pressing cylinder 1302 from the pressing cylinder placement position 1304 to place the pressing cylinder 1302 on the PCR tube 1704. After the fluorescent PCR test is completed, the PCR gripper 1501 can grip the pressing cylinder 1302 to place the pressing cylinder 1302 in the pressing cylinder placement position 1304, grip the PCR tube 1704 after the test to move the PCR tube 1704 to a PCR-tube discard port 1305 for discarding. Then the PCR gripper 1501 can grip the pressing cylinder 1302 from the pressing cylinder placement position 1304 to put the pressing cylinder 1302 back to the original position.

In addition, it should be noted that, the nucleic acid extraction and fluorescent PCR test system according to the present application includes a frame and also the devices arranged on the frame including the extraction-strip loading device 2, the sample-holder loading device 3, the extraction-strip transfer gripper 4, the sealing-film piercing device 7, the filling device 8, the low-temperature lysis device 9, the magnetic-bead washing device 10, the high-temperature dissociation device 11, the refined-solution magnetic-absorption device 6, the discard device 18, the consumable supply device 17, the refrigeration-reagent supply device 16, the reagent needle 12, the PCR-tube transfer device 14, the PCR-tube transfer gripper 15 and the fluorescent PCR test device 13. These devices are integrated into one system, so that the system is highly integrated and can achieve automatic extraction of nucleic acid and automatic tests of fluorescent PCR.

The system achieves the automatic loading of the extraction reagent by the extraction-strip loading device 2; achieves the automatic loading and unloading of the sample, to be tested, by the sample-holder loading device 3; achieves the automatic extraction of the nucleic acid by the extraction-strip transfer gripper 4, the sealing-film piercing device 7, the filling device 8, the low-temperature lysis device 9, the magnetic-bead washing device 10, the high-temperature dissociation device 11, the refined-solution magnetic-absorption device 6, the discard device 18, the consumable supply device 17, the refrigeration-reagent supply device 16, and the filling device 8; and achieves the automatic test of fluorescent PCR of nucleic acid by the PCR-tube transfer device 14, the PCR-tube transfer gripper 15 and the fluorescent PCR test device 13.

The system supports the instant on-line test of samples to be tested, and is provided with multiple independent temperature control components and photometry assemblies to support the simultaneous on-line test of multiple items, and achieves the function of random test and on-demand test of a single sample or multiple samples to be tested. The waiting time for test of the sample is effectively reduced. In addition, the nucleic acid extraction and the fluorescent PCR test of this system are performed without human, so that the system is highly automated, which can effectively avoid human errors during test, improve the test efficiency and lower the labor intensity.

It should be noted that, as used in the first passage 201, the second passage 202, the first pushing device 203, the second pushing device 204, the first magnet, the second magnet, the first forward-backward pusher 803, the second forward-backward pusher 901, the third forward-backward pusher 1101, the fourth forward-backward pusher 1004, and the fifth forward-backward pusher 1803, the ordinal terms “first”, “second”, “third”, “fourth”, and “fifth” are only for distinguishing different positions, and do not imply a sequence in priority.

In addition, it should be further noted that the orientation or positional relationships indicated by the terms “front”, “rear”, “up”, “down” and the like are based on illustrations in the drawings, and are merely for simplification of description and ease of understanding, rather than indicating or implying that the device or element referred to must have a particular orientation or be constructed and operated in the particular orientation, and therefore should not be construed as a limit to the present application.

The embodiments in this specification are described in a progressive manner. Each embodiment focuses on differences from other embodiments, and for the same or similar parts among the embodiments, reference can be made to one another. Any combination of all the embodiments provided in the present application is within the scope of protection of the present application, and will not be described herein.

The nucleic acid extraction and fluorescent PCR test system is described in detail above. The principle and the embodiments of the present application are illustrated herein through specific examples. The description of the above embodiments is merely used to facilitate understanding the method and core idea of the present application. It should be noted that for those skilled in the art, various improvements and modifications can be made to the present application without departing from the principle of the present application, and these modifications and improvements are also deemed to fall into the scope of protection of the present application defined by the appended claims.

The invention claimed is:

1. A nucleic acid extraction and fluorescent PCR test system, comprising: an extraction strip, an extraction-strip loading device which has a function of on-line adding the extraction strip and is configured to load the extraction strip, a sample-holder loading device which is configured to load and unload a sample, an extraction-strip transfer gripper which is configured to drive the extraction strip to move to a preset position, a nucleic-acid extraction device which is configured to refine the sample to obtain nucleic acid, a PCR test device which is configured to perform a fluorescent PCR test on the nucleic acid, and a control device;

wherein the extraction-strip loading device, the sample-holder loading device, the extraction-strip transfer gripper, the nucleic-acid extraction device and the PCR test device are connected to the control device, wherein the PCR test device comprises a fluorescent PCR test device which is configured to perform fluorescent PCR tests on a sealed PCR tube; and the fluorescent PCR test device is connected to the control device, wherein the fluorescent PCR test device comprises: a housing, a photometry assembly and temperature control components, wherein the housing is provided with a plurality of test positions for placing the sealed PCR, and each of the plurality of test positions is provided with the corresponding temperature control component, so that the temperatures in the plurality of test positions are independently controlled to rise or fall; wherein the photometry assembly and the temperature control components are both connected to the control device; and the photometry assembly comprises a light source assembly which is configured to provide a test light source and a driving component which is configured to drive the light source assembly to move; the number of the light source assembly is plural, the plurality of light source assemblies provide different types of light sources, and each light source assembly illuminates, driven by the driving component, the corresponding test position.

2. The nucleic acid extraction and fluorescent PCR test system according to claim 1, wherein the extraction-strip loading device comprises: a passage and a pushing device which is configured to push the extraction strip to move in the passage;

wherein one end of the passage is a gripping position for the extraction strip, the pushing device is movable transversely, and the pushing device is connected to the control device.

3. The nucleic acid extraction and fluorescent PCR test system according to claim 2, wherein the gripping position is provided with a jacking device which is configured to move up and down to separate the extraction strip, and the jacking device is connected to the control device.

4. The nucleic acid extraction and fluorescent PCR test system according to claim 1, wherein the sample-holder loading device comprises: a sample holder which is configured to load the sample, a loading pusher, an emergency pusher, a scanner, a transfer pusher and an unloading pusher, wherein the transfer pusher is configured to transfer the sample to a scanning position of the scanner and to move the sample after scanning to a sampling position, and the unloading pusher is configured to convey the sample after sampling to a sample recovery area; and the loading pusher, the emergency pusher, the scanner, the transfer pusher, and the unloading pusher are all connected to the control device.

5. The nucleic acid extraction and fluorescent PCR test system according to claim 1, wherein the extraction-strip transfer gripper comprises: an openable gripper device which is configured to grip the extraction strip, a gripper lifting device which is configured to drive the gripper device to move up and down, and a gripper transverse-movement device which is configured to drive the gripper lifting device to move transversely, wherein the gripper device is arranged on the gripper lifting device, and the gripper lifting device is slidably connected with the gripper transverse-movement device; and the gripper device, the gripper lifting device and the gripper transverse-movement device are all connected to the control device.

6. The nucleic acid extraction and fluorescent PCR test system according to claim 1, wherein the nucleic-acid extraction device comprises: a sealing-film piercing device which is configured to pierce through a sealing film of the extraction strip, a filling device which is configured to add the sample to be tested to the extraction strip, a reagent needle, a magnetic-bead washing device, a high-temperature dissociation device which is configured to perform high-temperature incubation on the sample, and a refined-solution magnetic-absorption device which is configured to perform magnetic absorption refinement on the sample to obtain a nucleic acid refined solution; and the reagent needle is configured to add a corresponding reagent into the extraction strip or a PCR tube and to add the nucleic acid refined solution of the extraction strip into the PCR tube.

7. The nucleic acid extraction and fluorescent PCR test system according to claim 6, wherein the sealing-film piercing device comprises: a piercer and a driving assembly, wherein the driving assembly is connected with the piercer to drive the piercer to move; and when the piercer moves to a piercing position, the piercer pierces through the sealing film of the extraction strip; and the driving assembly is connected to the control device.

8. The nucleic acid extraction and fluorescent PCR test system according to claim 6, wherein the filling device comprises: a sample needle which is configured to draw the sample and a sample moving device which is configured to drive the sample needle to move in space, wherein the sample needle is connected to the sample moving device, and the sample moving device is connected to the control device.

9. The nucleic acid extraction and fluorescent PCR test system according to claim 6, wherein the high-temperature dissociation device comprises an incubation heating block which is configured to heat a reaction chamber of the extraction strip, and the incubation heating block is connected to the control device.

10. The nucleic acid extraction and fluorescent PCR test system according to claim 6, wherein the magnetic-bead washing device comprises: a detergent needle, a detergent driving device which is configured to drive the detergent needle to move in space, a magnet device which is configured to selectively apply a magnetic field to the reaction chamber of the extraction strip, and a magnet driving device which is configured to drive the magnet device to rotate;

wherein the magnet driving device is connected to the magnet device, and the detergent needle is connected to the detergent driving device; and the magnet driving device and the detergent driving device are both connected to the control device.

11. The nucleic acid extraction and fluorescent PCR test system according to claim 1, further comprising a refrigeration-reagent supply device which has a refrigeration function and is configured to provide different reagents.

12. The nucleic acid extraction and fluorescent PCR test system according to claim 1, further comprising a discard device which is configured to recycle the discarded extraction strip, wherein the discard device is connected to the control device.

* * * * *